United States Patent
Höfgen et al.

(10) Patent No.: US 7,550,465 B2
(45) Date of Patent: Jun. 23, 2009

(54) PYRIDO[3,2-E]PYRAZINES, THEIR USE AS INHIBITORS OF PHOSPHODIESTERASE 10, AND PROCESSES FOR PREPARING THEM

(75) Inventors: Norbert Höfgen, Ottendorf-Okrills (DE); Hans Stange, Riesa (DE); Barbara Langen, Radebaul (DE); Ute Egerland, Radebeul (DE); Rudolf Schindler, Dresden (DE); Thomas Pfeifer, Radebeul (DE); Chris Rundfeldt, Coswig (DE)

(73) Assignee: Elbion GmbH, Radebeul (DE)

( * ) Notice: Subject to any disclaimer, the term of this patent is extended or adjusted under 35 U.S.C. 154(b) by 29 days.

(21) Appl. No.: 11/753,207

(22) Filed: May 24, 2007

(65) Prior Publication Data

US 2008/0027064 A1  Jan. 31, 2008

Related U.S. Application Data

(60) Provisional application No. 60/809,242, filed on May 30, 2006.

(51) Int. Cl.
*A61K 31/4985* (2006.01)
(52) U.S. Cl. .......................... 514/250; 544/346
(58) Field of Classification Search .................. 544/346
See application file for complete search history.

(56) References Cited

U.S. PATENT DOCUMENTS

2003/0032579 A1  2/2003  Lebel

FOREIGN PATENT DOCUMENTS

EP  1 250 923 A  10/2002

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*

* cited by examiner

*Primary Examiner*—James O Wilson
*Assistant Examiner*—Brian McDowell
(74) *Attorney, Agent, or Firm*—Fulbright & Jaworski L.L.P.

(57) ABSTRACT

The invention relates to pyrido[3,2-e]pyrazines, to processes for preparing them, to pharmaceutical preparations which comprise these compounds and to the pharmaceutical use of these compounds, which are inhibitors of phosphodiesterase 10, as active compounds for treating diseases of mammals including a human which can be influenced by using the compounds according to the invention to inhibit phosphodiesterase 10 activity in the central nervous system. More particularly, the invention relates to the treatment of neurologic and psychiatric disorders, for example psychosis and disorders comprising cognitive deficits as symptoms.

11 Claims, 10 Drawing Sheets

Figure 1

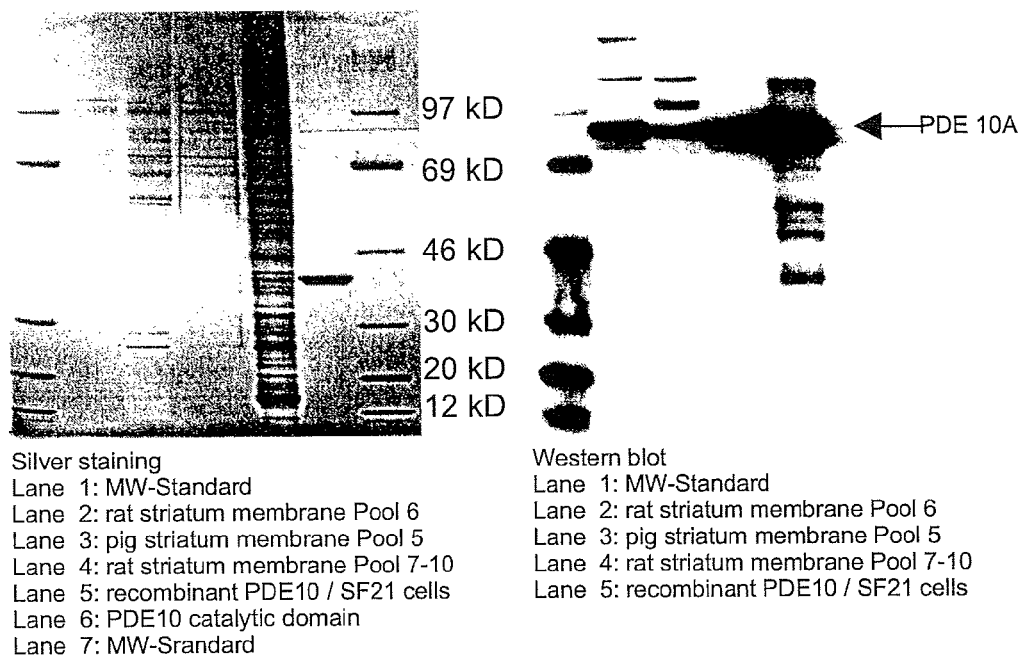

Silver staining
Lane 1: MW-Standard
Lane 2: rat striatum membrane Pool 6
Lane 3: pig striatum membrane Pool 5
Lane 4: rat striatum membrane Pool 7-10
Lane 5: recombinant PDE10 / SF21 cells
Lane 6: PDE10 catalytic domain
Lane 7: MW-Srandard Western blot
Lane 1: MW-Standard
Lane 2: rat striatum membrane Pool 6
Lane 3: pig striatum membrane Pool 5
Lane 4: rat striatum membrane Pool 7-10
Lane 5: recombinant PDE10 / SF21 cells

Figure 3/1

Page1

```
                                                                                          Section 1
                          (1) 1         10        20        30        40          56
PDE10 rat cat domain      (1) ------------------------------------------------ACCTCTGA
PDE10 guinea pig P4-P3    (1) --------------------------------------------------------
PDE10 pig P1-P2           (1) TGCATCTACAGGGTTACCATGGAGAAGCTGTCCTACCACAGCATTTGTACCGCGGA
Consensus                 (1)                                                 ACC C GA
                                                                                          Section 2
                         (57) 57        70        80        90        100       112
PDE10 rat cat domain      (9) GGAATGGCAAGGCCTCATGCACTTCAACTTGCCAGCACGCATCTGCCGGGACATCG
PDE10 guinea pig P4-P3    (1) --------------------------------------------------------
PDE10 pig P1-P2          (57) AGAGTGGCAAGGCCTCATGCGCTTCAACCTTCCCGTCCGTCTTTGCAAGGAGATTG
Consensus                (57)  GA TGGCAAGGCCTCATGC CTTCAAC T CC G  CG  T TGC  GGA AT G
                                                                                          Section 3
                        (113) 113       120       130       140       150       168
PDE10 rat cat domain     (65) AGCTATTCCACTTTGACATTGGTCCTTTCGAGAACATGTGGCCTGGGATCTTTGTC
PDE10 guinea pig P4-P3    (1) --------------------------------------------------------
PDE10 pig P1-P2         (113) AATTGTTCCACTTCGACATTGGTCCTTTTGAAAACATGTGGCCTGGAATCTTTGTC
Consensus               (113) A  T TTCCACTT GACATTGGTCCTTT GA AACATGTGGCCTGG ATCTTTGTC
                                                                                          Section 4
                        (169) 169       180       190       200       210       224
PDE10 rat cat domain    (121) TACATGATCCATCGGTCTTGTGGGACATCCTGTTTTGAACTTGAAAAATTGTGCCG
PDE10 guinea pig P4-P3    (1) --------------------------------------------------------
PDE10 pig P1-P2         (169) TATATGGTTCATCGCTTCTGTGGGACGGCCTGCTTTGAGCTTGAAAAGCTGTGTCG
Consensus               (169) TA ATG T CATCG T  TGTGGGAC  CCTG TTTGA CTTGAAAA  TGTG CG
                                                                                          Section 5
                        (225) 225       230       240       250       260       270   280
PDE10 rat cat domain    (177) TTTTATCATGTCTGTGAAGAAGAACTATAGGCGGGTTCCTTACCACAACTGGAAGC
PDE10 guinea pig P4-P3    (1) ----------CTGTCAAGAAGAACTATCGGCGGGTTCCTTACCACAACTGGAAGC
PDE10 pig P1-P2         (225) TTTTATCATGTCTGTGAAGAAGAACTATCGTCGGGTTCCTTACCACAACTGGAAGC
Consensus               (225) TTTTATCATGTCTGTGAAGAAGAACTATCGGCGGGTTCCTTACCACAACTGGAAGC
                                                                                          Section 6
                        (281) 281       290       300       310       320       336
PDE10 rat cat domain    (233) ATGCAGTCACGGTGGCGCACTGCATGTACGCCATACTTCAAAACAACAATGGCCTC
PDE10 guinea pig P4-P3   (46) ATGCAGTCACGGTGGCGCACTGCATGTACGCCATACTTCAAAACAACAATGGCCTC
PDE10 pig P1-P2         (281) ACGCGGTCACGGTGGCACACTGCATGTACGCCATCCTCCAGAACAGCCACGGGCTC
Consensus               (281) ATGCAGTCACGGTGGCGCACTGCATGTACGCCATACTTCAAAACAACAATGGCCTC
                                                                                          Section 7
                        (337) 337       350       360       370       380       392
PDE10 rat cat domain    (289) TTCACAGACCTTGAGCGCAAAGGCCTGCTAATTGCCTGTCTGTGCCATGACCTGGA
PDE10 guinea pig P4-P3  (102) TTCACAGACCTTGAGCGCAAAGGCCTGCTAATTGCCTGTCTGTGCCATGACCTGGA
PDE10 pig P1-P2         (337) TTCACCGACCTCGAGCGCAAAGGACTGCTAATCGCGTGTCTGTGCCACGACCTGGA
Consensus               (337) TTCACAGACCTTGAGCGCAAAGGCCTGCTAATTGCCTGTCTGTGCCATGACCTGGA
                                                                                          Section 8
                        (393) 393       400       410       420       430       448
PDE10 rat cat domain    (345) CCACAGGGGCTTCAGTAACAGCTACCTGCAGAAATTCGACCACCCCCTGGCTGCGT
PDE10 guinea pig P4-P3  (158) CCACAGGGGCTTCAGTAACAGCTACCTGCAGAAATTCGACCACCCCCTGGCTGCGT
PDE10 pig P1-P2         (393) CCACAGGGGCTTCAGCAACAGCTACCTGCAGAAATTCGACCACCCCCTGGCCGCTC
Consensus               (393) CCACAGGGGCTTCAGTAACAGCTACCTGCAGAAATTCGACCACCCCCTGGCTGCGT
```

Figure 3/2

Page2

```
                                                                                          Section 9
                         (449) 449       460       470       480       490       504
   PDE10 rat cat domain  (401) TGTACTCCACCTCCACCATGGAGCAACACCACTTCTCCCAGACGGTGTCCATCCTC
 PDE10 guinea pig P4-P3  (214) TGTACTCCACCTCCACCATGGAGCAACACCACTTCTCCCAGACGGTGTTCATCCTC
      PDE10 pig P1-P2    (449) TCTACTCCACGCCCACCATGGAGCAGCACCACTTCTCCCAGACCGTGTCCATCCTC
             Consensus   (449) TGTACTCCACCTCCACCATGGAGCAACACCACTTCTCCCAGACGGTGTCCATCCTC
                                                                                          Section 10
                         (505) 505   510       520       530       540       550       560
   PDE10 rat cat domain  (457) CAGCTGGAAGGACACAACATCTTCTCCACCCTGAGCTCCAGCGAGTACGAGCAGGT
 PDE10 guinea pig P4-P3  (270) CAGCTGGAAGGACACAACATCTTCTCCACCCTGAGCTCCAGCGAGTACGAGCAGGT
      PDE10 pig P1-P2    (505) CAGTTGGAAGGGCACAACATCTTCTCCACCCTGAGCTCCAGTGAGTACGAGCAGGT
             Consensus   (505) CAGCTGGAAGGACACAACATCTTCTCCACCCTGAGCTCCAGCGAGTACGAGCAGGT
                                                                                          Section 11
                         (561) 561       570       580       590       600       616
   PDE10 rat cat domain  (513) GCTGGAGATCATCCGCAAAGCCATCATCGCCACTGACCTCGCACTGTACTTTGGGA
 PDE10 guinea pig P4-P3  (326) GCTGGAGATCATCCGCAAAGCCATCATTGCCACAGACCTCGCACTGTACTTTGCGA
      PDE10 pig P1-P2    (561) GCTTGAGATCATCCGCAAAGCCATCATTGCCACAGACCTGCTTTGTACTTTGGAA
             Consensus   (561) GCTGGAGATCATCCGCAAAGCCATCATCGCCACTGACCTCGCACTGTACTTTGGGA
                                                                                          Section 12
                         (617) 617       630       640       650       660       672
   PDE10 rat cat domain  (569) ACAGGAAGCAGTTGGAGGAGATGTACCAGACAGGGTCGCTGAACCTCCACAACCAG
 PDE10 guinea pig P4-P3  (382) ACAGGAAGCAGTTGGAGGAGATGTACCAGACAGGGTCGCTGAACCTCAATAACCAG
      PDE10 pig P1-P2    (617) ACAGGAAACAGTTGGAGGAGATGTACCAGACCGGATCGCTAAACCTTAATAACCAG
             Consensus   (617) ACAGGAAGCAGTTGGAGGAGATGTACCAGACAGGGTCGCTGAACCTCAATAACCAG
                                                                                          Section 13
                         (673) 673       680       690       700       710       728
   PDE10 rat cat domain  (625) TCCCATCGAGACCGCGTCATCGGCTTGATGATGACTGCCTGCGATCTTTGCTCTGT
 PDE10 guinea pig P4-P3  (438) TCCCATCGAGACCGCGTCATCGGCTTGATGATGACTGCCTGCGATCTTTGCTCTGT
      PDE10 pig P1-P2    (673) TCACATAGAGACCGCGTCATTGGTTTGATGATGACTGCCTGTGATCTCTGTTCCGT
             Consensus   (673) TCCCATCGAGACCGCGTCATCGGCTTGATGATGACTGCCTGCGATCTTTGCTCTGT
                                                                                          Section 14
                         (729) 729       740       750       760       770       784
   PDE10 rat cat domain  (681) GACGAAACTATGGCCAGTTACAAAATTGACAGCAAATGATATATATGCAGAGTTCT
 PDE10 guinea pig P4-P3  (494) GACGAAACTATGGCCAGTTACAAAATTGACAGCAAATGATATATATGCAGAGTTCT
      PDE10 pig P1-P2    (729) GACAAAACTGTGGCCAGTAACAAAACTGACGGCAAATGATATATATGCGGAATTCT
             Consensus   (729) GACGAAACTATGGCCAGTTACAAAATTGACAGCAAATGATATATATGCAGAGTTCT
                                                                                          Section 15
                         (785) 785   790       800       810       820       830       840
   PDE10 rat cat domain  (737) GGGCTGAGGGGGATGAGATGAAGAAGTTGGGGATACAGCCCATCCCTATGATGGAC
 PDE10 guinea pig P4-P3  (550) GGGCTGAGGGGGATGAGATGAAGAAGTTGGGGATACAGCCCATCCCTATGATGGAC
      PDE10 pig P1-P2    (785) GGGCCGAGGGCGATGAGGTGAAGAAGCTGGGAATACAGCCTATTCCCATGATGGAC
             Consensus   (785) GGGCTGAGGGGGATGAGATGAAGAAGTTGGGGATACAGCCCATCCCTATGATGGAC
                                                                                          Section 16
                         (841) 841       850       860       870       880       896
   PDE10 rat cat domain  (793) AGAGACAAGCGAGATGAAGTCCCTCAAGGACAGCTTGGATTCTACAATGCTGTGGC
 PDE10 guinea pig P4-P3  (606) AGAGACAAGAAGGATGAAGTCCCTCAAGGACCAGCTTCGGATTCTACAACGCGGTAGC
      PDE10 pig P1-P2    (841) AGAGACAAGAAGGACGAAGTCCCCACAAGGCCAGCTCGGATTCTACAACGCGGTAGC
             Consensus   (841) AGAGACAAGAAGGATGAAGTCCCTCAAGGACAGCTTGGATTCTACAATGCTGTGGC
```

Figure 3/3

Page3

```
                                                                                             Section 17
                    (897) 897         910         920         930         940         952
PDE10 rat cat domain (849) CATCCCCTGCTATACCACCCTGACGCAGATCCTCCCACCCACAGAGCCTCTGCTGA
PDE10 guinea pig P4-P3 (662) CATCCCCTGCTATACCACCCTGACGCAGATCCTCCCACCCACAGAGCCTCTGCTGA
PDE10 pig P1-P2     (897) TATCCCCTGCTACACCACCCTCACCCAGATCTTCCCGCCCACAGAGCCTCTTCTGA
          Consensus (897) CATCCCCTGCTATACCACCCTGACGCAGATCCTCCCACCCACAGAGCCTCTGCTGA
                                                                                             Section 18
                    (953) 953         960         970         980         990         1008
PDE10 rat cat domain (905) AGGCCTGCAGGGATAACCTCAATCAGTGGGAGAAGGTAATTCGAGGGGAAGAGACA
PDE10 guinea pig P4-P3 (718) AGGCCTGCAGGGATAACCTCAATCAGTGGGAGAAGGTAATTCGAGGGGAAGAGACA
PDE10 pig P1-P2     (953) AGGCCTGCAGGGATA-----------------------------------------
          Consensus (953) AGGCCTGCAGGGATAACCTCAATCAGTGGGAGAAGGTAATTCGAGGGGAAGAGACA
                                                                                             Section 19
                    (1009) 1009        1020        1030        1040        1050        1064
PDE10 rat cat domain (961) GCAATGTGGATTTCAGGCCCAGCAACTAGCAAAAGCACATCTGAGAAGCCGACCAG
PDE10 guinea pig P4-P3 (774) GCAATGTGGATTTCAGGCCCAGCAACTAGCAAAAGCACATCAGGGAAGCCGACCAG
PDE10 pig P1-P2     (968) --------------------------------------------------------
          Consensus (1009) GCAATGTGGATTTCAGGCCCAGCAACTAGCAAAAGCACATC G GAAGCCGACCAG
                                                                                             Section 20
                    (1065) 1065   1070    1080
PDE10 rat cat domain (1017) GAAGGTCGATGACTGA
PDE10 guinea pig P4-P3 (830) GAAGGTCGATGACTGA
PDE10 pig P1-P2     (968) ----------------
          Consensus (1065) GAAGGTCGATGACTGA
```

Figure 4

```
                                                                                              Section 1
                    (1) 1         10        20        30        40           58
PDE10 rat cat domain (1) ------------------TAEEWQGLMHFNLPARICRDIELFHFDIGPFENMWPGIF
    PDE10A guinea pig (1) ----------------------------------------------------------
          PDE10A pig (1) IRLCIYRVTMEKLSYHSICTAEEWQGLMRFNLPVRLCKEIELFHFDIGPFENMWPGIF
           Consensus (1)                     TAEEWQGLM FNLP RICKDIELFHFDIGPFENMWPGIF
                                                                                              Section 2
                   (59) 59        70        80        90        100          116
PDE10 rat cat domain (40) VYMIHRSCGTSCFELEKLCRFIMSVKKNYRRVPYHNWKHAVTVAHCMYAILQNNNGLF
   PDE10A guinea pig  (1) ---------------------VKKNYRRVPYHNWKHAVTVAHCMYAILQNNNGLF
         PDE10A pig (59) VYMVHRFCGTACFELEKLCRFIMSVKKNYRRVPYHNWKHAVTVAHCMYAILQNSHGLF
          Consensus (59) VYMIHR CGTACFELEKLCRFIMSVKKNYRRVPYHNWKHAVTVAHCMYAILQNNNGLF
                                                                                              Section 3
                  (117) 117       130       140       150       160          174
PDE10 rat cat domain (98) TDLERKGLLIACLCHDLDHRGFSNSYLQKFDHPLAALYSTSTMEQHHFSQTVSILQLE
  PDE10A guinea pig (35) TDLERKGLLIACLCHDLDHRGFSNSYLQKFDHPLAALYSTSTMEQHHFSQTVFILQLE
        PDE10A pig (117) TDLERKGLLIACLCHDLDHRGFSNSYLQKFDHPLAALYSTPTMEQHHFSQTVSILQLE
         Consensus (117) TDLERKGLLIACLCHDLDHRGFSNSYLQKFDHPLAALYSTSTMEQHHFSQTVSILQLE
                                                                                              Section 4
                  (175) 175       180       190       200       210       220   232
PDE10 rat cat domain (156) GHNIFSTLSSSEYEQVLEIIRKAIIATDLALYFGNRKQLEEMYQTGSLNLNNQSHRDR
  PDE10A guinea pig (93)  GHNIFSTLSSSEYEQVLEIIRKAIIATDLALYFGNRKQLEEMYQTGSLNLNNQSHRDR
        PDE10A pig (175) GHNIFSTLSSSEYEQVLEIIRKAIIATDLALYFGNRKQLEEMYQTGSLNLNNQSHRDR
         Consensus (175) GHNIFSTLSSSEYEQVLEIIRKAIIATDLALYFGNRKQLEEMYQTGSLNLNNQSHRDR
                                                                                              Section 5
                  (233) 233       240       250       260       270       280   290
PDE10 rat cat domain (214) VIGLMMTACDLCSVTKLWPVTKLTANDIYAEFWAEGDEMKKLGIQPIPMMDRDKRDEV
  PDE10A guinea pig (151) VIGLMMTACDLCSVTKLWPVTKLTANDIYAEFWAEGDEMKKLGIQPIPMMDRDKKDEV
        PDE10A pig (233) VIGLMMTACDLCSVTKLWPVTKLTANDIYAEFWAEGDEVKKLGIQPIPMMDRDKKDEV
         Consensus (233) VIGLMMTACDLCSVTKLWPVTKLTANDIYAEFWAEGDEMKKLGIQPIPMMDRDKKDEV
                                                                                              Section 6
                  (291) 291       300       310       320       330          348
PDE10 rat cat domain (272) PQGQLGFYNAVAIPCYTTLTQILPPTEPLLKACRDNLNQWEKVIRGEETAMWISGPAT
  PDE10A guinea pig (209) PQGQLGFYNAVAIPCYTTLTQILPPTEPLLKACRDNLNQWEKVIRGEETAMWISGPAT
        PDE10A pig (291) PQGQLGFYNAVAIPCYTTLTQIFPPTEPLLKACRDKAEF-------------------
         Consensus (291) PQGQLGFYNAVAIPCYTTLTQILPPTEPLLKACRDNLNQWEKVIRGEETAMWISGPAT
                                                                                              Section 7
                  (349) 349           362
PDE10 rat cat domain (330) SKSTSEKPTRKVDD
  PDE10A guinea pig (267) SKSTSGKPTRKVDD
        PDE10A pig (330) --------------
         Consensus (349) SKSTS KPTRKVDD
```

PYRIDO[3,2-E]PYRAZINES, THEIR USE AS INHIBITORS OF PHOSPHODIESTERASE 10, AND PROCESSES FOR PREPARING THEM

This application claims priority from provisional U.S. Ser. No. 60/809,242 filed May 30, 2006, herein incorporated by reference in its entirety.

FIELD OF THE INVENTION

The invention relates to pyrido[3,2-e]pyrazines, to processes for preparing them, to pharmaceutical preparations which comprise these compounds and to the pharmaceutical use of these compounds, which are inhibitors of phosphodiesterase 10, as active compounds for treating diseases of mammals including a human which can be influenced by using the compounds according to the invention to inhibit phosphodiesterase 10 activity in the central nervous system. More particularly, the invention relates to the treatment of neurologic and psychiatric disorders, for example psychosis and disorders comprising cognitive deficits as symptoms.

BACKGROUND

Psychotic disorders, especially schizophrenia, are severe mental disorders which extremely impair daily life. The symptoms of psychosis may be divided into two fractions. In the acute phase, it is predominated by hallucinations and delusions being called the positive symptoms. When the agitated phase abates the so called negative symptoms become obvious. They include cognitive deficits, social phobia, reduced vigilance, indifference and deficits in verbal learning and memory, verbal fluency and motor function.

Although several antipsychotics are available since, the present therapy of psychosis is not satisfactory. The classic antipsychotics, such as haloperidol, with a high affinity to dopamine D2 receptor show extreme side effects, such extrapyramidal symptoms (=EPS) and do not improve the negative symptoms of schizophrenia so that they do not enable the patient to return to everyday life.

Clozapine which has emerged as a benchmark therapeutic ameliorating positive, negative and cognitive symptoms of schizophrenia and devoid of EPS shows agranulocytosis as a major, potential lethal side-effect (Capuano et al., 2002). Besides, there is still a high amount of therapy resistant cases (Lindenmayer et al., 2002).

In conclusion, there is still a need for developing new antipsychotics which ameliorate positive, negative and cognitive symptoms of psychosis and have a better side effect profile.

The exact pathomechanism of psychosis is not yet known. A dysfunction of several nreurotransmitter systems has been shown. The two major neurotransmitter systems that are involved are the dopaminergic and the glutamatergic system:

Thus, acute psychotic symptoms may be stimulated by dopaminergic drugs (Capuano et al., 2002) and classical antipsychotics, like haloperidol, have a high affinity to the dopamine D2 receptor (Nyberg et al., 2002). Animal models based on a hyperactivity of the dopaminergic neurotransmitter system (amphetamine hyperactivity, apomorphine climbing) are used to mimic the positive symptoms of schizophrenia.

Additional there is growing evidence that the glutamatergic neurotransmitter system plays an important role in the development of schizophrenia (Millan, 2005). Thus, NMDA antagonists like phencyclidine and ketamine are able to stimulate schizophrenic symptoms in humans and rodents (Abi-Saab et al., 1998; Lahti et al., 2001). Acute administration of phencyclidine and MK-801 induce hyperactivity, stereotypies and ataxia in rats mimicking psychotic symptoms. Moreover, in contrast to the dopaminergic models the animal models of psychosis based on NMDA antagonists do not only mimic the positive symptoms but also the negative and cognitive symptoms of psychosis (Abi-Saab et al., 1998; Jentsch and Roth, 1999). Thus, NMDA antagonists, additionally induce cognitive deficits and social interaction deficits.

Eleven families of phosphodiesterases have been identified in mammals so far (Essayan, 2001). The role of PDEs in the cell signal cascade is to inactivate the cyclic nucleotides cAMP and/or cGMP (Soderling and Beavo, 2000). Since cAMP and cGMP are important second messenger in the signal cascade of G-protein-coupled receptors PDEs are involved in a broad range of physiological mechanisms playing a role in the homeostasis of the organism.

The PDE families differ in their substrate specificity for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is primarily expressed in the brain and here in the nucleus accumbens and the caudate putamen. Areas with moderate expression are the thalamus, hippocampus, frontal cortex and olfactory tubercle (Menniti et al., 2001). All these brain areas are described to participate in the pathomechanism of schizophrenia (Lapiz et al. 2003) so that the location of the enzyme indicates a predominate role in the pathomechanism of psychosis.

In the striatum PDE10A is predominately found in the medium spiny neurons and there are primarily associated to the postsynaptic membranes of these neurons (Xie et al., 2006). By this location PDE10A may have an important influence on the signal cascade induced by dopaminergic and glutamatergic input on the medium spiny neurons two neurotransmitter systems playing a predominate role in the pathomechanism of psychosis.

Phosphodiesterase (PDE) OA, in particular, hydrolyses both cAMP and cGMP having a higher affinity for cAMP ($K_m$=0.05 µM) than for cGMP ($K_M$=3 µM) (Sonderling et al., 1999).

Psychotic patients have been shown to have a dysfunction of cGMP and cAMP levels and its downstream substrates (Kaiya, 1992; Muly, 2002; Garver et al., 1982). Additionally, haloperidol treatment has been associated with increased cAMP and cGMP levels in rats and patients, respectively (Leveque et al., 2000; Gattaz et al., 1984). As PDE10 hydrolyses both cAMP and cGMP (Kotera et al., 1999) an inhibition of PDE10A would also induce an increase of cAMP and cGMP and thereby having a similar effect on cyclic nucleotide levels as haloperidol.

The antipsychotic potential of PDE10A inhibitors is further supported by studies of Kostowski et al. (1976) who showed that papaverine, a moderate selective PDE10A inhibitor, reduces apomorphine-induced stereotypies in rats, an animal model of psychosis, and increases haloperidol-induced catalepsy in rats while concurrently reducing dopamine concentration in rat brain. Activities that are also seen with classical antipsychotics. This is further supported by a patent application establishing papaverine as a PDE10A inhibitor for the treatment of psychosis (US Patent Application No. 2003/0032579).

In addition to classical antipsychotics which mainly ameliorate the positive symptoms of psychosis PDE10A also bears the potential to improve the negative and cognitive symptoms of psychosis.

Focusing on the dopaminergic input on the medium spiny neurons PDE10A inhibitors by up-regulating cAMP and cGMP levels act as D1 agonists and D2 antagonists because the activation of Gs-protein coupled dopamine D1 receptor increases intracellular cAMP, whereas the activation of the Gi-protein coupled dopamine D2 receptor decreases intracellular cAMP levels through inhibition of adenylyl cyclase activity (Mutschler et al., 2001).

Elevated intracellular cAMP levels mediated by D1 receptor signalling seems to modulate a series of neuronal processes responsible for working memory in the prefrontal cortex (Sawaguchi, 2000), and it is reported that D1 receptor activation may improve working memory deficits in schizophrenic patients (Castner et al., 2000). Thus, it seems likely that a further enhancement of this pathway might also improve the cognitive symptoms of schizophrenia.

Further indication of an effect of PDE10A inhibition on negative symptoms of psychosis are given by Rodefer et al. (2005) who could show that papaverine reverses attentional set-shifting deficits induced by subchronic administration of phencyclidine, an NMDA antagonist, in rats. Attentional deficits including an impairment of shifting attention to novel stimuli belongs to the negative symptoms of schizophrenia. In the study the attentional deficits were induced by administering phencyclidine for 7 days followed by a washout period. The PDE10A inhibitor papaverine was able to reverse the enduring deficits induced by the subchronic treatment.

Imidazo[1,5-a]pyrido[3,2-e]pyrazinones its synthesis and some medical uses are well described in patents and the literature.

The applications EP 0 400 583 and U.S. Pat. No. 5,055,465 from Berlex Laboratories, Inc. disclose a group of imidazoquinoxalinones, their aza analogs and a process for their preparation. These compounds have been found to have inodilatory, vasodilatory and venodilatory effects. The therapeutic activity is based on the inhibition of phosphodiesterase 3 (PDE3).

EP 0 736 532 discloses pyrido[3,2-e]pyrazinones and a process for their preparation. These compounds are described to have anti-asthmatic and anti-allergic properties. Examples of this invention are inhibitors of PDE4 and PDE5.

WO 00/43392 discloses the use of imidazo[1,5-a]pyrido[3,2-e]pyrazinones which are inhibitors of PDE3 and PDE5 for the therapy of erectile dysfunction, heart failure, pulmonic hypertonia and vascular diseases which are accompanied by insufficient blood supply.

An other group of pyrido[3,2-e]pyrazinones, disclosed in WO 01/68097 are inhibitors of PDE5 and can be used for the treatment of erectile dysfunction.

Further methods for the preparation of imidazo[1,5-a]pyrido[3,2-e]pyrazinones are described also by D. Norris et al. (Tetrahedron Letters 42 (2001), 4297-4299).

WO 92/22552 refers to imidazo[1,5-a]quinoxalines which are generally substituted at position 3 with a carboxylic acid group and derivatives thereof. These compounds are described to be useful as anxiolytic and sedative/hypnotic agents.

In contrast only a limited number of imidazo[1,5-a]pyrido[3,2-e]pyrazines and their medical use are already published.

WO 99/45009 describes a group of imidazopyrazines of formula (I)

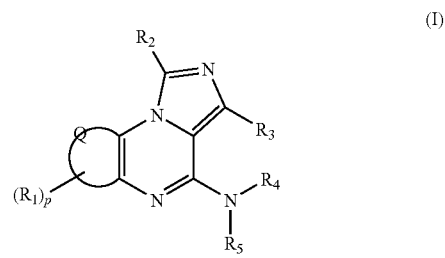

(I)

Part of the definition of Q is to form a 6-membered heterocyclic ring including pyridin. While $R_1$, $R_2$ and $R_3$ are representing a large variety of substituents the definition of the group —$NR_4R_5$ is of special importance.

$R_4$ and $R_5$ are each independently hydrogen, $R_6$ or —C(O) $R_6$ or the whole group $NR_4R_5$ forms a 3- to 8-membered saturated or unsaturated ring.

$R_6$ is alkyl, alkenyl, alkynyl, cycloalkyl, cycloalkylalkyl, cycloalkenyl, cycloalkenylalkyl, aryl, aralkyl, heterocyclo or heterocycloalkyl, each of which is unsubstituted or substituted.

These compounds are described to be inhibitors of protein tyrosine kinases used in the treatment of protein tyrosine kinase-associated disorders such as immunologic disorders.

Interestingly, for all examples listed in claim 9 the structure of the group $NR_4R_5$ is limited in a way that one of $R_4$ and $R_5$ is hydrogen and for the other one $R_6$ is phenyl (unsubstituted or substituted).

This structural selection of the group $NR_4R_5$ is inline with published SAR data from the same company (P. Chen et al., Bioorg. Med. Chem. Lett. 12 (2002), 1361-1364 and P. Chen et al., Bioorg. Med. Chem. Lett. 12 (2002), 3153-3156).

SUMMARY OF THE INVENTION

This invention relates to compounds of formula (II) and to pharmaceutically acceptable salts, solvates and prodrugs thereof.

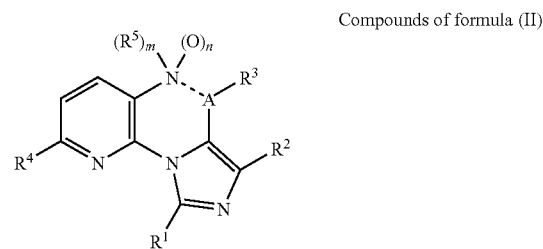

Compounds of formula (II)

wherein the bond between A and N is a single bond or a double bond,

A is C when the bond is a double bond and CH when the bond is a single bond, m is 0 or 1, n is 0 or 1, wherein $R^1$ and $R^2$ are independently selected from

H, a cyclic radical, $C_{1-8}$ alkyl, optionally mono- or polysubstituted with halo, OH, O—$C_{1-3}$ alkyl and/or a cyclic radical, $C_{2-8}$ alkenyl, optionally mono- or polysubstituted with halo, OH, O—$C_{1-3}$ alkyl and/or a cyclic-radical, $C_{2-8}$ alkynyl, optionally mono- or polysubstituted with halo, OH, O—$C_{1-3}$-alkyl and/or a cyclic radical, a saturated, monounsaturated or polyunsaturated carboxylic ring system with 3 to 8 atoms, e.g. phenyl, or a heterocyclic ring system with 5 to 15 ring atoms containing at least one heteroatom selected from N including N-oxide, O and S, each optionally mono- or polysubstituted with halo, amino, $C_{1-3}$ alkylamino, di-$C_{1-3}$ alkylamino, nitro, $C_{1-3}$ alkyl, O—$C_{1-3}$ alkyl, and/or a cyclic radical, and $R^3$ is selected from

H, a cyclic radical, $N_3$,

CN, $R^6$, $OR^6$, $SR^6$, $SOR^6$, $SO_2R^6$, $NH(CO)OR^6$, $N((CO)OR^6)_2$, $NR^6((CO)OR^6)$,

NH—(C=O)—$NH_2$, $NR^6$—(C=O)—$NH_2$,

NH—(C=O)—$NHR^6$, $NR^6$—(C=O)—$NHR^6$,

NH—$SO_2R^6$, $N(SO_2R^6)_2$, and $NR^6(SO_2R^6)$, wherein $R^6$ is in each case independently, a cyclic radical, $C_{1-8}$ alkyl, $C_{3-8}$ cyclo(hetero)alkyl, $C_{2-8}$ alkenyl, $C_{3-8}$ cyclo(hetero)alkenyl, or $C_{2-8}$ alkynyl each optionally mono or polysubstituted with halo, OH and/or O—$C_{1-3}$alkyl; and/or a cyclic radical, $R^7$, $OR^7$, $SR^7$, $NHSO_2R^7$, $N(SO_2R^7)_2$, or $N(R^8)SO_2R^7$, wherein $R^7$ is aryl, heteroaryl, aryl-$C_{1-5}$ alkyl, heteroaryl-$C_{1-5}$ alkyl, wherein aryl is phenyl or naphthyl, heteroaryl is an aromatic heterocyclic ring system of 5 to 15 ring atoms containing at least one atom selected from N including N-oxide, S, and O and wherein aryl and heteroaryl are optionally mono- or polysubstituted with halo, amino, $C_{1-3}$ alkylamino, di-$C_{1-3}$ alkylamino, nitro, $C_{1-3}$ alkyl, O—$C_{1-3}$ alkyl and/or a cyclic radical, $R^8$ is $C_{1-5}$ alkyl, optionally mono or polysubstituted with halo, OH, O—$C_{1-3}$ alkyl and/or a cyclic radical, $R^4$ is selected from

H, halo, a cyclic radical, $R^9$,

OH or $OR^9$,

NH(C=O)—$C_{1-3}$ alkyl, optionally mono- or polysubstituted with halo, OH, O—$C_{1-3}$ alkyl and/or a cyclic radical or $NH_2$, $NHR^9$ or $NR^9R^{10}$, wherein $R^9$ and $R^{10}$ are independently selected from a cyclic radical, $C_{1-6}$ alkyl or $C_{3-6}$ cyclo(hetero)alkyl, optionally mono- or polysubstituted with halo, OH, O—$C_{1-3}$ alkyl and/or a cyclic radical, aryl-$C_{1-5}$-alkyl wherein aryl is phenyl, optionally mono- or polysubstituted with halo, amino, $C_{1-3}$ alkylamino, di-$C_{1-3}$ alkylamino, nitro, $C_{1-3}$ alkyl, OH, O—$C_{1-3}$ alkyl and/or a cyclic radical, or $NR^9R^{10}$ together form a saturated or unsaturated five-, six- or seven-membered ring which can contain up to 3 heteroatoms, preferably N including —N-oxide, S and/or O, optionally mono- or polysubstituted with halo, amino, $C_{1-3}$ alkylamino, di-$C_{1-3}$ alkylamino, $C_{1-3}$ alkyl, O—$C_{1-3}$ alkyl and/or aryl-$C_{1-5}$-alkyl, wherein aryl is phenyl, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl and/or a cyclic radical, and $R^5$ is selected from

H, $C_{1-5}$ alkyl, $C_{3-6}$ cycloalkyl or (CO)—$C_{1-5}$ alkyl, optionally mono or polysubstituted with halo, OH, O—$C_{1-3}$ alkyl and/or a cyclic radical, or pharmaceutically acceptable salts and derivatives thereof.

BRIEF DESCRIPTION OF THE FIGURES

FIG. 1 shows PDE10 detection with specific antibodies by Western blot.

FIG. 3 shows the gene alignment of rat, guinea pig and pig PDE10 catalytic domains.

FIG. 4 is a protein alignment showing difference in the protein sequences without the catalytic domain of PDE10 for rat, guinea pig and pig.

DETAILED DESCRIPTION

Figure 2:
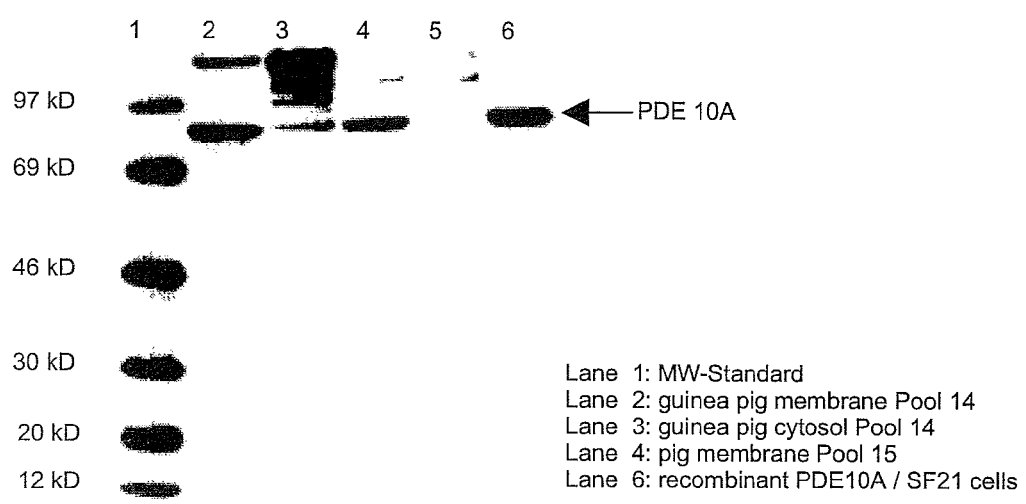
FIG. 2 shows that the main part of the protein PDE10 was found in the membrane fraction.

The term "halo" refers to fluoro, chloro, bromo or iodo.

The terms "alkyl", "alkenyl" and "alkynyl" refer to straight or branched radicals with up to 8 carbon atoms preferably up to 6 carbon atoms and more preferably up to 5 carbon atoms such as methyl, ethyl, vinyl, ethynyl, propyl, allyl, propynyl, butyl, butenyl, butynyl etcl. which may optionally be substituted as indicated above.

The terms "cyclo(hetero)alkyl" and "cyclo(hetero)alkyenyl" refer to cyclic radicals' which may optionally contain one or more heteroatoms selected from N including N-oxide, O and S, which may optionally be substituted as indicated above.

The term "cyclic radical" refers to saturated, unsaturated or aromatic carbocyles or carboheterocycles, optionally mono- or polysubstituted with halo, amino, $C_{1-3}$ alkylamino, di-$C_{1-3}$ alkylamino, nitro, $C_{1-3}$ alkyl, OH, O—$C_{1-3}$ alkyl and/or a cyclic radical. The cyclic radical preferably contains 3 to 20, in particular 4 to 10 C-atoms. Carboheterocycles may contain 1 to 6, in particular 1 to 3 heteroatoms, preferably selected from O, N, S and/or P. The cyclic radical can be bound via a C-atom or optionally via a N, O, S, SO or $SO_2$-group. An example for a cyclic radical is phenyl.

A preferred embodiment of this invention relates to compounds of formula (II) wherein the bond between A and N is a double bond.

An other preferred embodiment of this invention relates to compounds of formula (II) wherein m and n are both 0.

A further preferred embodiment of this invention relates to compounds of formula (II) wherein $R^1$ is selected from

H, $C_{1-4}$ alkyl, particularly $C_{2-4}$ alkyl optionally mono- or polysubstituted with halo, OH, O—$C_{1-3}$ alkyl and/or a cyclic radical or phenyl, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl and/or a cyclic radical.

Especially preferred are $C_{2-4}$-alkyl, e.g. propyl such as n-propyl or i-propyl, or phenyl, optionally substituted.

A further preferred embodiment of this invention relates to compounds of formula (II) wherein $R^2$ is
H or
$C_{1-4}$ alkyl, particularly methyl, optionally substituted, e.g. halo substituted.

Especially preferred are hydrogen, a methyl group or a trifluoromethyl group.

A further preferred embodiment of this invention relates to compounds of formula (II) wherein $R^3$ is H, CN or $C_{1-3}$ alkyl, e.g. methyl.

A further preferred embodiment of this invention relates to compounds of formula (II) wherein $R^3$ is NH—(C=O)$OR^6$, particularly NH—(C=O)—$OC_{1-5}$ alkyl, optionally mono- or polysubstituted as indicated above.

A further preferred embodiment of this invention relates to compounds of formula (II) wherein $R^3$ is NH—$SO_2R^6$, particularly NH—$SO_2$—$C_{1-5}$ alkyl, optionally mono- or polysubstituted as indicated above.

A further preferred embodiment of this invention relates to compounds of formula (II) wherein $R^4$ is selected from H, $C_{1-3}$ alkyl, O—$C_{1-3}$ alkyl, $NH_2$, $NHC_{1-3}$ alkyl, wherein alkyl is optionally mono- or polysubstituted with halo, OH, O—$C_{1-3}$ alkyl and/or a cyclic radical or NH(C=O)—$C_{1-3}$ alkyl, optionally mono- or polysubstituted with halo, OH, O—$C_{1-3}$ alkyl and/or a cyclic radical or
 cyclopropyl, cyclobutyl, tetrahydropyrrolyl, pyrrolyl, pyrazolyl, imidazolyl, 1,2,3-triazolyl, 1,2,4-triazolyl, piperidinyl, morpholinyl, piperazinyl, optionally mono- or polysubstituted with halo, OH, $C_{1-5}$ alkyl and/or O—$C_{1-3}$ alkyl, or aryl-$C_{1-5}$-alkyl, wherein aryl is phenyl, optionally mono- or polysubstituted with halo, amino, $C_{1-3}$ alkylamino, di-$C_{1-3}$ alkylamino, nitro, $C_{1-3}$ alkyl, O—$C_{1-3}$ alkyl and/or a cyclic radical, for example

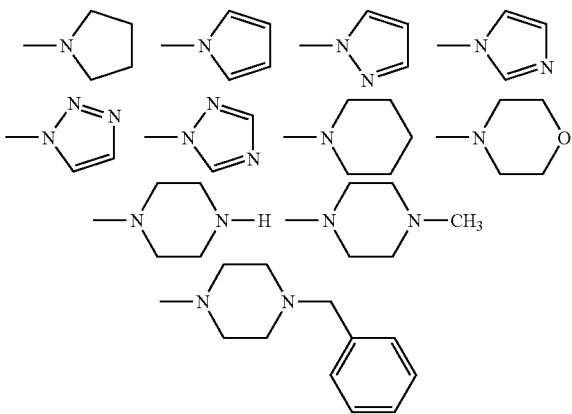

A further especially preferred embodiment of this invention relates to compounds of formula (II), wherein $R^4$ is H, $C_{1-3}$ alkyl or O—$C_{1-3}$ alkyl, particularly H or $OCH_3$.

Examples of specific compounds of the formula (II) are the following:
4,8-dimethoxy-3-methyl-1-propyl-imidazo[1,5-a]pyrido[3,2-e]pyrazine
4,8-dimethoxy-1-propyl-imidazo[1,5-a]pyrido[3,2-e]pyrazine
4,8-dimethoxy-1-ethyl-3-methyl-imidazo[1,5-a]pyrido[3,2-e]pyrazine
4,8-dimethoxy-1,3-dimethyl-imidazo[1,5-a]pyrido[3,2-e]pyrazine
4,8-dimethoxy-3-methyl-imidazo[1,5-a]pyrido[3,2-e]pyrazine
1-ethyl-4-isopropyloxy-8-methoxy-3-methyl-imidazo[1,5-a]pyrido[3,2-e]pyrazine
1-ethyl-8-methoxy-3-methyl-4-propyloxy-imidazo[1,5-a]pyrido[3,2-e]pyrazine
4-cyclopentyloxy-1-ethyl-8-methoxy-3-methyl-imidazo[1,5-a]pyrido[3,2-e]pyrazine
4-isopropyloxy-8-methoxy-3-methyl-1-propyl-imidazo[1,5-a]pyrido[3,2-e]pyrazine
8-methoxy-1,3-dimethyl-4-(2,3,6-trifluorobenzyloxy)-imidazo[1,5-a]pyrido[3,2-e]pyrazine
4-(2,4-dichlorobenzyloxy)-1-ethyl-8-methoxy-3-methyl-imidazo[1,5-a]pyrido[3,2-e]pyrazine
4-(2-chloro-6-fluorobenzyloxy)-1-ethyl-8-methoxy-3-methyl-imidazo[1,5-a]pyrido[3,2-e]pyrazine
1-ethyl-8-methoxy-3-methyl-4-(2,3,6-trifluorobenzyloxy)-imidazo[1,5-a]pyrido[3,2-e]pyrazine
1-ethyl-8-methoxy-3-methyl-4-(2,4,6-trimethylbenzyloxy)-imidazo[1,5-a]pyrido[3,2-e]pyrazine
4-(2-chloro-6-fluorobenzyloxy)-8-methoxy-3-methyl-1-propyl-imidazo[1,5-a]pyrido[3,2-e]pyrazine
4-(2,6-difluorobenzyloxy)-8-methoxy-3-methyl-1-propyl-imidazo[1,5-a]pyrido[3,2-e]pyrazine
1-ethyl-8-methoxy-3-methyl-4-(2-phenylethyloxy)-imidazo[1,5-a]pyrido[3,2-e]pyrazine
8-methoxy-3-methyl-4-(2-phenylethyloxy)-1-propyl-imidazo[1,5-a]pyrido[3,2-e]pyrazine
8-methoxy-1,3-dimethyl-4-(2-phenylethyloxy)-imidazo[1,5-a]pyrido[3,2-e]pyrazine
8-methoxy-3-methyl-4-(2-phenylethyloxy)-imidazo[1,5-a]pyrido[3,2-e]pyrazine
8-methoxy-3-methyl-4-(3-phenylpropyloxy)-1-propyl-imidazo[1,5-a]pyrido[3,2-e]pyrazine
1-ethyl-8-methoxy-3-methyl-4-(3-phenylpropyloxy)-imidazo[1,5-a]pyrido[3,2-e]pyrazine
1,3-dimethyl-8-methoxy-4-(3-phenylpropyloxy)-imidazo[1,5-a]pyrido[3,2-e]pyrazine
4-[(3,5-dimethylisoxazol-4-yl)methyloxy]-1-ethyl-8-methoxy-3-methyl-imidazo[1,5-a]pyrido[3,2-e]pyrazine
1-ethyl-8-methoxy-3-methyl-4-methylthio-imidazo[1,5-a]pyrido[3,2-e]pyrazine
8-methoxy-3-methyl-4-methylthio-1-propyl-imidazo[1,5-a]pyrido[3,2-e]pyrazine
1,3-dimethyl-8-methoxy-4-methylthio-imidazo[1,5-a]pyrido[3,2-e]pyrazine
8-methoxy-3-methyl-4-methylthio-imidazo[1,5-a]pyrido[3,2-e]pyrazine
4-cyano-8-methoxy-3-methyl-1-propyl-imidazo[1,5-a]pyrido[3,2-e]pyrazine
4-cyano-8-methoxy-3-methyl-1-ethyl-imidazo[1,5-a]pyrido[3,2-e]pyrazine
4-azido-8-methoxy-3-methyl-1-propyl-imidazo[1,5-a]pyrido[3,2-e]pyrazine
8-methoxy-3-methyl-4-methylsulfinyl-1-propyl-imidazo[1,5-a]pyrido[3,2-e]pyrazine
8-methoxy-3-methyl-4-methylsulfonyl-1-propyl-imidazo[1,5-a]pyrido[3,2-e]pyrazine
1-ethyl-8-methoxy-3-methyl-4-methylsulfinyl-imidazo[1,5-a]pyrido[3,2-e]pyrazine
8-methoxy-3-methyl-1-propyl-imidazo[1,5-a]pyrido[3,2-e]pyrazine
1-ethyl-8-methoxy-3-methyl-imidazo[1,5-a]pyrido[3,2-e]pyrazine
4-ethyl-8-methoxy-3-methyl-1-propyl-imidazo[1,5-a]pyrido[3,2-e]pyrazine 3,4-dimethyl-8-methoxy-1-propyl-imidazo[1,5-a]pyrido[3,2-e]pyrazine
3,4-dimethyl-8-methoxy-1-propyl-imidazo[1,5-a]pyrido[3,2-e]pyrazine hydrochloride
1-ethyl-3,4-dimethyl-8-methoxy-imidazo[1,5-a]pyrido[3,2-e]pyrazine
1,3,4-trimethyl-8-methoxy-imidazo[1,5-a]pyrido[3,2-e]pyrazine
3,4-dimethyl-8-methoxy-1-(3,3,3-trifluoropropyl)-imidazo[1,5-a]pyrido[3,2-e]pyrazine
3,4-dimethyl-8-methoxy-1-pentyl-imidazo[1,5-a]pyrido[3,2-e]pyrazine
1-cyclohexyl-3,4-dimethyl-8-methoxy-imidazo[1,5-a]pyrido[3,2-e]pyrazine
3,4-dimethyl-1-hexyl-8-methoxy-imidazo[1,5-a]pyrido[3,2-e]pyrazine
3,4-dimethyl-8-methoxy-1-phenethyl-imidazo[1,5-a]pyrido[3,2-e]pyrazine
3,4-dimethyl-8-methoxy-1-phenyl-imidazo[1,5-a]pyrido[3,2-e]pyrazine
3,4-dimethyl-8-methoxy-1-phenyl-imidazo[1,5-a]pyrido[3,2-e]pyrazine dihydrochloride
3,4-dimethyl-8-methoxy-1-(2-chlorophenyl)-imidazo[1,5-a]pyrido[3,2-e]pyrazine
3,4-dimethyl-8-methoxy-1-(4-fluorophenyl)-imidazo[1,5-a]pyrido[3,2-e]pyrazine
1-propyl-3,4,8-trimethyl-imidazo[1,5-a]pyrido[3,2-e]pyrazine
1-propyl-3,4-dimethyl-imidazo[1,5-a]pyrido[3,2-e]pyrazine
1-propyl-4,8-dimethyl-imidazo[1,5-a]pyrido[3,2-e]pyrazine
8-difluoromethoxy-3,4-dimethyl-1-propyl-imidazo[1,5-a]pyrido[3,2-e]pyrazine
3,4-dimethyl-8-(piperidin-1-yl)-methoxy-1-propyl-imidazo[1,5-a]pyrido[3,2-e]pyrazine
3,4-dimethyl-8-(4-methyl-piperazin-1-yl)-methoxy-1-propyl-imidazo[1,5-a]pyrido[3,2-e]pyrazine
3,4-dimethyl-8-(2-ethyl-4-methyl-imidazol-1-yl)-methoxy-1-propyl-imidazo[1,5-a]pyrido[3,2-e]pyrazine
3,4-dimethyl-8-(2-propyl-4-methyl-imidazol-1-yl)-methoxy-1-propyl-imidazo[1,5-a]pyrido[3,2-e]pyrazine
4-difluoromethoxy-3-methyl-1-propyl-imidazo[1,5-a]pyrido[3,2-e]pyrazine-8-ol
8-methoxy-3-methyl-5-oxo-1-propyl-imidazo[1,5-a]pyrido[3,2-e]pyrazine
3,4-dimethyl-8-methoxy-5-oxo-1-propyl-imidazo[1,5-a]pyrido[3,2-e]pyrazine
8-methoxy-4-methoxycarbonylamino-3-methyl-1-propyl-imidazo[1,5-a]pyrido[3,2-e]pyrazine
4-ethoxycarbonylamino-8-methoxy-3-methyl-1-propyl-imidazo[1,5-a]pyrido[3,2-e]pyrazine
4-(N,N-bis-methoxycarbonyl)-amino-8-methoxy-3-methyl-1-propyl-imidazo[1,5-a]pyrido[3,2-e]pyrazine
8-methoxy-4-(methoxycarbonyl-methyl-amino)-3-methyl-1-propyl-imidazo[1,5-a]pyrido[3,2-e]pyrazine
8-methoxy-3-methyl-4-(3-methyl-ureido)-1-propyl-imidazo[1,5-a]pyrido[3,2-e]pyrazine
8-methoxy-3-methyl-1-propyl-4-ureido-imidazo[1,5-a]pyrido[3,2-e]pyrazine
8-methoxy-3-methyl-4-(3-isopropyl-ureido)-1-propyl-imidazo[1,5-a]pyrido[3,2-e]pyrazine
8-methoxy-3-methyl-4-methylsulfonylamino-1-propyl-imidazo[1,5-a]pyrido[3,2-e]pyrazine
4-(N,N-bis-methylsulfonyl)-amino-8-methoxy-3-methyl-1-propyl-imidazo[1,5-a]pyrido[3,2-e]pyrazine
4-ethylsulfonylamino-8-methoxy-3-methyl-1-propyl-imidazo[1,5-a]pyrido[3,2-e]pyrazine
1-ethyl-8-methoxy-3-methyl-4-methylsulfonylamino-imidazo[1,5-a]pyrido[3,2-e]pyrazine
8-methoxy-3-methyl-1-propyl-4-trifluoromethylsulfonylamino-imidazo[1,5a]pyrido[3,2-e]pyrazine
8-methoxy-3-methyl-1-propyl-4-propylsulfonylamino-imidazo[1,5-a]pyrido[3,2-e]pyrazine
4-isopropylsulfonylamino-8-methoxy-3-methyl-1-propyl-imidazo[1,5-a]pyrido[3,2-e]pyrazine
8-methoxy-3-methyl-4-(4-methylphenylsulfonylamino)-1-propyl-imidazo[1,5-a]pyrido[3,2-e]pyrazine
4-[N,N-bis-(4-methylphenylsulfonyl)-amino]-8-methoxy-3-methyl-1-propyl-imidazo[1,5-a]pyrido[3,2-e]pyrazine
8-methoxy-3-methyl-1-(3,3,3-trifluoropropyl)-4-methylsulfonylamino-imidazo[1,5-a]pyrido[3,2-e]pyrazine
1-hexyl-8-methoxy-3-methyl-4-methylsulfonylamino-imidazo[1,5-a]pyrido[3,2-e]pyrazine
8-methoxy-3-methyl-1-phenethyl-4-methylsulfonylamino-imidazo[1,5-a]pyrido[3,2-e]pyrazine
8-methoxy-3-methyl-1-phenyl-4-methylsulfonylamino-imidazo[1,5-a]pyrido[3,2-e]pyrazine
1-(2-chlorophenyl)-8-methoxy-3-methyl-4-methylsulfonylamino-imidazo[1,5-a]pyrido[3,2-e]pyrazine
1-(4-fluorophenyl)-8-methoxy-3-methyl-4-methylsulfonylamino-imidazo[1,5-a]pyrido[3,2-e]pyrazine
3-methyl-8-(4-methyl-2-propyl-imidazol-1-yl)-1-propyl-4-methylsulfonylamino-imidazo[1,5-a]pyrido[3,2-e]pyrazine
3-methyl-4-methylsulfonylamino-1-propyl-imidazo[1,5-a]pyrido[3,2-e]pyrazin-8-ol hydrobromide
3-methyl-4-methylsulfonylamino-1-propyl-imidazo[1,5-a]pyrido[3,2-e]pyrazin-8-ol
8-difluoromethoxy-3-methyl-4-methylsulfonylamino-1-propyl-imidazo[1,5-a]pyrido[3,2-e]pyrazine
8-cyclopropylmethoxy-3-methyl-4-methylsulfonylamino-1-propyl-imidazo[1,5-a]pyrido[3,2-e]pyrazine
3-methyl-1-propyl-4,5-dihydro-imidazo[1,5-a]pyrido[3,2-e]pyrazine
8-methoxy-1-propyl-4,5-dihydro-imidazo[1,5-a]pyrido[3,2-e]pyrazine
8-methoxy-3-methyl-1-propyl-4,5-dihydro-imidazo[1,5-a]pyrido[3,2-e]pyrazine
8-methoxy-3-methyl-1-propyl-4,5-dihydro-imidazo[1,5-a]pyrido[3,2-e]pyrazine hydrochloride
1-ethyl-8-methoxy-3-methyl-4,5-dihydro-imidazo[1,5-a]pyrido[3,2-e]pyrazine
3,5-dimethyl-8-methoxy-1-propyl-4,5-dihydro-imidazo[1,5-a]pyrido[3,2-e]pyrazine
5-acetyl-8-methoxy-3-methyl-1-propyl-4,5-dihydro-imidazo[1,5-a]pyrido[3,2-e]pyrazine and their pharmaceutically acceptable salts and derivatives thereof.

Especially preferred, the compound of formula (II) is selected from 3,4-dimethyl-8-methoxy-1-propyl-imidazo[1,5-a]-pyrido[3,2-e]-pyrazine and pharmaceutically acceptable salts and derivatives thereof.

The invention furthermore relates to the physiologically acceptable salts, solvates and derivatives of the compounds according to formula (II). Derivatives of the compounds according to formula (II) are, for example, amides, esters and ethers. Further, the term "derivative" also encompasses prodrugs and metabolites of compounds of formula (II).

The physiologically acceptable salts may be obtained by neutralizing the bases with inorganic or organic acids or by neutralizing the acids with inorganic or organic bases. Examples of suitable inorganic acids are hydrochloric acid, sulphuric acid, phosphoric acid or hydrobromic acid, while examples of suitable organic acids are carboxylic acid, sulpho acid or sulphonic acid, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, maleic acid, salicylic acid, 3-aminosalicylic acid, ascorbic acid, embonic acid, nicotinic acid, isonicotinic acid, oxalic acid, gluconic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid. Examples of suitable inorganic bases are sodium hydroxide, potassium hydroxide and ammonia, while examples of suitable organic bases are amines, preferably, however, tertiary amines, such as trimethylamine, triethylamine, pyridine, N,N-dimethylaniline, quinoline, isoquinoline, α-picoline, β-picoline, γ-picoline, quinaldine and pyrimidine.

In addition, physiologically acceptable salts of the compounds according to formula (II) can be obtained by converting derivatives which possess tertiary amino groups into the corresponding quaternary ammonium salts in a manner known per se using quaternizing agents. Examples of suitable quaternizing agents are alkyl halides, such as methyl iodide, ethyl bromide and n-propyl chloride, and also arylalkyl halides, such as benzyl chloride or 2-phenylethyl bromide.

Furthermore, in the case of the compounds of the formula (II) which contain an asymmetric carbon atom, the invention relates to the D form, the L form and D,L mixtures and also, where more than one asymmetric carbon atom is present, to the diastereomeric forms. Those compounds of the formula (II) which contain asymmetric carbon atoms, and which as a rule accrue as racemates, can be separated into the optically active isomers in a known manner, for example using an optically active acid. However, it is also possible to use an optically active starting substance from the outset, with a corresponding optically active or diastereomeric compound then being obtained as the end product.

The compounds according to the invention have been found to have pharmacologically important properties which can be used therapeutically. The compounds according to formula (II) can be used alone, in combination with each other or in combination with other active compounds. The compounds according to the invention are inhibitors of phosphodiesterase 10. It is therefore a part of the subject-matter of this invention that the compounds according to formula (II), and their salts and also pharmaceutical preparations which comprise these compounds or their salts, can be used for treating or preventing disorders associated with, accompanied by and/or covered by phosphodiesterase hyperactivity and/or disorders in which inhibiting phosphodiesterase 10 is of value.

Surprisingly, the compounds of formula (II) are potent inhibitors of the enzyme PDE10.

It is an embodiment of this invention, that compounds of formula (II) including their salts, solvates and prodrugs and also pharmaceutical compositions comprising an amount of a compound of formula (II) or one of its salts, solvates or prodrugs effective in inhibiting PDE10 can be used for the treatment of central nervous system disorders of mammals including a human.

More particularly, the invention relates to the treatment of neurological and psychiatric disorders including, but not limited to, (1) schizophrenia and other psychotic disorders; (2) mood [affective] disorders; (3) neurotic, stress-related and somatoform disorders including anxiety disorders; (4) eating disorders; sexual dysfunction comprising excessive sexual drive; (5) disorders of adult personality and behaviour; (6) disorders usually first diagnosed in infancy, childhood and adolescence; (7) mental retardation and (8) disorders of psychological development; (9) disorders comprising the symptom of cognitive deficiency in a mammal, including a human; (10) factitious disorders.

(1) Examples of schizophrenia and other psychotic disorders disorders that can be treated according to the present invention include, but are not limited to, continuous or episodic schizophrenia of different types (for instance paranoid, hebephrenic, catatonic, undifferentiated, residual, and schizophreniform disorders); schizotypal disorders (such as borderline, latent, prepsychotic, prodromal, pseudoneurotic pseudopsychopathic schizophrenia and schizotypal personality disorder); persistent delusional disorders; acute, transient and persistent psychotic disorders; induced delusional disorders; schizoaffective disorders of different type (for instance manic depressive or mixed type); puerperal psychosis and other and unspecified nonorganic psychosis.

(2) Examples of mood [affective] disorders that can be treated according to the present invention include, but are not limited to, manic episodes associated to bipolar disorder and single manic episodes, hypomania, mania with psychotic symptoms; bipolar affective disorders (including for instance bipolar affective disorders with current hypomanic and manic episodes with or without psychotic symptoms); depressive disorders, such as single episode or recurrent major depressive disorder, depressive disorder with postpartum onset, depressive disorders with psychotic symptoms; persistent mood [affective] disorders, such as cyclothymia, dysthymia; premenstrual dysphoric disorder.

(3) Examples of disorders belonging to the neurotic, stress-related and somatoform disorders that can be treated according to the present invention include, but are not limited to, phobic anxiety disorders, for instance agoraphobia and social phobia primarily but not exclusively related to psychosis; other anxiety disorders such as panic disorders and general anxiety disorders; obsessive compulsive disorder; reaction to sever stress and adjustment disorders, such as post traumatic stress disorder; dissociative disorders and other neurotic disorders such as depersonalisation-derealisation syndrome.

(5) Examples of disorders of adult personality and behaviour that can be treated according to the present invention include, but are not limited to, specific personality disorders of the paranoid, schizoid, schizotypal, antisocial, borderline, histrionic, narcissistic, avoidant, dissocial, emotionally unstable, anankastic, anxious and dependent type; mixed personality disorders; habit and impulse disorders (such as trichotillomania, pyromania, maladaptive aggression); disorders of sexual preference.

(6) Examples of disorders usually first diagnosed in infancy, childhood and adolescence that can be treated according to the present invention include, but are not limited to, hyperkinetic disorders, attentional deficit/hyperactivity disorder (AD/HD), conduct disorders; mixed disorders of conduct and emotional disorders; nonorganic enuresis, nonorganic encopresis; stereotyped movement disorder; and other specified behavioural emotional disorders, such as attention deficit disorder without hyperactivity, excessive masturbation nail-biting, nose-picking and thumb-sucking; disorders of psychological development particularly schizoid disorder of childhood and pervasive development disorders such as psychotic episodes associated to Asperger's syndrome.

(8) Examples of disorders of psychological development include but are not limited to developmental disorders of speech and language, developmental disorders of scholastic skills, such as specific disorder of arithmetical skills, reading disorders and spelling disorders and other learning disorders. These disorders are predominantly diagnosed in infancy, childhood and adolescence.

(9) The phrase "cognitive deficiency" as used here in "disorder comprising as a symptom cognitive deficiency" refers to a subnormal functioning or a suboptimal functioning in one or more cognitive aspects such as memory, intellect, learning and logic ability, or attention in a particular individual comparative to other individuals within the same general age population.

(10) Examples of disorders comprising as a symptom cognitive deficiency that can be treated according to the present invention include, but are not limited to, cognitive deficits primarily but not exclusively related to psychosis; age-associated memory impairment, Parkinson's disease, Alzheimer's disease, multi infarct dementia, Lewis body dementia, stroke, frontotemporal dementia, progressive supranuclear palsy Huntington's disease and in HIV disease, cerebral trauma, drug abuse and mild cognitive disorder.

(11) Additionally, the invention relates to movement disorders with malfunction of basal ganglia. Examples of movement disorders with malfunction of basal ganglia that can be treated according to the present invention include, but are not limited to, different subtypes of dystonia, such as focal dystonias, multiple-focal or segmental dystonias, torsion dystonia, hemispheric, generalised and tardive dyskinesias (induced by psychopharmacological drugs), akathisias, dyskinesias such as Huntington's disease, Parkinson's disease, Lewis body disease, restless leg syndrome, PLMS.

(12) Furthermore the invention relates to the treatment of organic, including symptomatic mental disorders, especially to organic delusional (schizophrenia-like) disorders, presenil or senile psychosis associated to dementia, to psychosis in epilepsy and Parkinson's disease and other organic and symptomatic psychosis; delirium; infective psychosis; personality and behavioural disorders due to brain disease, damage and dysfunction.

(13) The invention relates to the treatment of mental and behavioural disorders due to psychoactive compounds, more particular to the treatment of psychotic disorders and residual and late-onset psychotic disorders induced by alcohol, opioids, cannabinoids, cocaine, hallucinogens, other stimulants, including caffeine, volatile solvents and other psychoactive compounds.

(14) The invention further relates to a general improvement of learning and memory capacities in a mammal, including a human.

An effective dose of the compounds according to the invention, or their salts, is used, in addition to physiologically acceptable carriers, diluents and/or adjuvants for producing a pharmaceutical composition. The dose of the active compounds can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001-2000 mg. Particular preference is given to administering daily doses of 0.1-500 mg, e.g. 0.1-100 mg.

Suitable administration forms are oral, parenteral, intravenous, transdermal, topical, inhalative, intranasal and sublingual preparations. Particular preference is given to using oral, parenteral, e.g. intravenous or intramuscular, intranasal preparations, e.g. dry powder or sublingual, of the compounds according to the invention. The customary galenic preparation forms, such as tablets, sugar-coated tablets, capsules, dispersible powders, granulates, aqueous solutions, alcohol-containing aqueous solutions, aqueous or oily suspensions, syrups, juices or drops, are used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators.

Examples of such additives are tartrate and citrate buffers, ethanol and sequestering agents (such as ethylenediaminetetraacetic acid and its non-toxic salts). High molecular weight polymers, such as liquid polyethylene oxides, microcrystalline celluloses, carboxymethyl celluloses, polyvinylpyrrolidones, dextrans or gelatine, are suitable for regulating the viscosity. Examples of solid carrier substances are starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats, and solid high molecular weight polymers, such as polyethylene glycol.

Oily suspensions for parenteral or topical applications can be vegetable synthetic or semisynthetic oils, such as liquid fatty acid esters having in each case from 8 to 22 C atoms in the fatty acid chains, for example palmitic acid, lauric acid, tridecanoic acid, margaric acid, stearic acid, arachidic acid, myristic acid, behenic acid, pentadecanoic acid, linoleic acid, elaidic acid, brasidic acid, erucic acid or oleic acid, which are esterified with monohydric to trihydric alcohols having from 1 to 6 C atoms, such as methanol, ethanol, propanol, butanol, pentanol or their isomers, glycol or glycerol. Examples of such fatty acid esters are commercially available miglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial ducktail gland fat, coconut fatty acid isopropyl ester, oleyl oleate, decyl oleate, ethyl lactate, dibutyl phthalate, diisopropyl adipate, polyol fatty acid esters, inter alia. Silicone oils of differing viscosity, or fatty alcohols, such as isotridecyl alcohol, 2-octyldodecanol, cetylstearyl alcohol or oleyl alcohol, or fatty acids, such as oleic acid, are also suitable. It is furthermore possible to use vegetable oils, such as castor oil, almond oil, olive oil, sesame oil, cotton seed oil, groundnut oil or soybean oil.

Suitable solvents, gelatinizing agents and solubilizers are water or water-miscible solvents. Examples of suitable substances are alcohols, such as ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, esters, morpholines, dioxane, dimethyl sulphoxide, dimethylformamide, tetrahydrofuran, cyclohexanone, etc.

Cellulose ethers which can dissolve or swell both in water or in organic solvents, such as hydroxypropylmethyl cellulose, methyl cellulose or ethyl cellulose, or soluble starches, can be used as film-forming agents.

Mixtures of gelatinizing agents and film-forming agents are also perfectly possible. In this case, use is made, in particular, of ionic macromolecules such as sodium carboxymethyl cellulose, polyacrylic acid, polymethacrylic acid and their salts, sodium amylopectin semiglycolate, alginic acid or propylene glycol alginate as the sodium salt, gum arabic, xanthan gum, guar gum or carrageenan. The following can be used as additional formulation aids: glycerol, paraffin of differing viscosity, triethanolamine, collagen, allantoin and novantisolic acid. Use of surfactants, emulsifiers or wetting agents, for example of Na lauryl sulphate, fatty alcohol ether sulphates, di-Na—N-lauryl-β-iminodipropionate, polyethoxylated castor oil or sorbitan monooleate, sorbitan monostearate, polysorbates (e.g. Tween), cetyl alcohol, lecithin, glycerol monostearate, polyoxyethylene stearate, alkylphenol polyglycol ethers, cetyltrimethylammonium chloride or mono-/dialkylpolyglycol ether orthophosphoric acid monoethanolamine salts can also be required for the formulation. Stabilizers, such as montmorillonites or colloidal silicic acids, for stabilizing emulsions or preventing the breakdown of active substances such as antioxidants, for example tocopherols or butylhydroxyanisole, or preservatives, such as p-hydroxybenzoic acid esters, can likewise be used for preparing the desired formulations.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

As indicated above, the compounds of the invention may be administered as a combination therapy with further active agents, e.g. therapeutically active compounds useful in the treatment of central nervous system disorders. These further compounds may be PDE10 inhibitors or compounds which have an activity which is not based on PDE10 inhibition such as dopamine D2 receptor modulating agents or NMDA modulating agents.

For a combination therapy, the active ingredients may be formulated as compositions containing several active ingredients in a single dose form and/or as kits containing individual active ingredients in separate dose forms. The active ingredients used in combination therapy may be co-administered or administered separately.

The synthesis of compounds of formula (II) preferably starts from imidazo[1,5-a]pyrido[3,2-e]pyrazinones of formula (III):

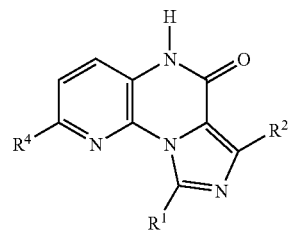

(III)

wherein $R^1$, $R^2$ and $R^4$ are as described above.

The preparation of compounds of formula (III) is well described e.g. in WO 00/43392, WO 01/68097 and also by D. Norris et al. (Tetrahedron Letters 42 (2001), 4297-4299).

According to standard procedures known from the literature and already used in WO 99/45009 compounds of formula (III) are halogenated by treatment with halogenating reagents like $POCl_3$, $PCl_3$, $PCl_5$ $SOCl_2$, $POBr_3$, $PBr_3$ or $PBr_5$, yielding e.g. 4-chloro or 4-bromo-imidazo[1,5-a]pyrido[3,2-e]pyrazines of formula (IV),

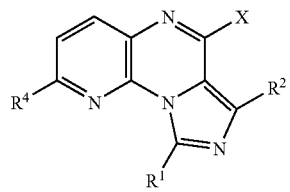

(IV)

wherein X is Cl or Br and $R^1$, $R^2$ and $R^4$ are as defined above.

Compounds of formula (II) where m and n are 0, the bond between A and N is a double bond and $R^3$ is selected from $OR^6$, $SR^6$, $OR^7$ or $SR^7$ as described above, are preferably prepared by the treatment of an intermediate of formula (IV) with the corresponding alcohols or mercaptanes $HOR^6$, $HOR^7$, $HSR^6$ or $HSR^7$.

EXAMPLES

Intermediate A1: 4-chloro-8-methoxy-3-methyl-1-propyl-imidazo[1,5-a]pyrido[3,2-e]pyrazine 16 g of 8-methoxy-3-methyl-1-propyl-imidazo[1,5-a]pyrido[3,2-e]pyrazine-4-one and 120 ml $POCl_3$ are mixed and heated up to reflux for 8 hours. After cooling to room temperature the reaction mixture is treated with 1200 ml crushed ice/water and stirred for 1 hour. The product is extracted with 2×300 ml dichloromethane. The collected organic layer is washed with 2×300 ml water and dried with $Na_2SO_4$. The solvent is removed under reduced pressure.

Yield: 14.5 g m.p.: 121-123° C.

Many other intermediates A of formula (IV) can be prepared according to this procedure. Some examples are the following:

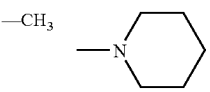

(IV)

| Intermediate | X | R¹ | R² | R⁴ | m.p. [° C.] |
|---|---|---|---|---|---|
| A1 | —Cl | —C₃H₇ | —CH₃ | —OCH₃ | 121-123 |
| A2 | —Cl | —C₂H₅ | —CH₃ | —OCH₃ | 148-150 |
| A3 | —Cl | —CH₃ | —CH₃ | —OCH₃ | 176-178 |
| A4 | —Cl | —C₆H₁₁ | —CH₃ | —OCH₃ | 211-213 |
| A5 | —Cl | —C₆H₁₃ | —CH₃ | —OCH₃ | 115-117 |
| A6 | —Cl | —C₅H₁₁ | —CH₃ | —OCH₃ | 110.5-113 |
| A7 | —Cl | —CH₂CH₂CF₃ | —CH₃ | —OCH₃ | 149-153 |
| A8 | —Cl | —(CH₂)₂C₆H₅ | —CH₃ | —OCH₃ | 130 |
| A9 | —Cl | —C₆H₅ | —CH₃ | —OCH₃ | 240-242 |
| A10 | —Cl | —C₆H₄(4-F) | —CH₃ | —OCH₃ | 256-258 |
| A11 | —Cl | —C₂H₅ | —CH₃ | —H | 117-120 |
| A12 | —Cl | —C₃H₇ | —CH₃ | —H | 138-140 |
| A13 | —Cl | —C₃H₇ | —H | —OCH₃ | 153-155 |
| A14 | —Cl | —CH(CH₃)₂ | —H | —OCH₃ | 162-164 |
| A15 | —Cl | —CH₃ | —H | —OCH₃ | 225-228 |
| A16 | —Cl | —H | —H | —H | 222-225 |
| A17 | —Cl | —H | —C₆H₅ | —OCH₃ | 168-171 |
| A18 | —Cl | —H | —CH₃ | —OCH₃ | 185-187 |
| A19 | —Cl | —C₃H₇ | —CH₃ | —CH₃ | 99-101 |
| A20 | —Cl | —C₂H₅ | —CH₃ | —N(C₂H₅)₂ | 145-150 |
| A21 | —Cl | —C₃H₇ | —CH₃ | 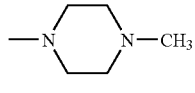 | |
| A22 | —Cl | —C₂H₅ | —CH₃ | 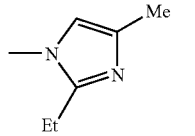 | 283-285 |
| A23 | —Cl | —C₂H₅ | —CH₃ | 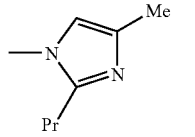 | 138-141 |
| A24 | —Cl | —C₃H₇ | —CH₃ | (imidazole with Me, Pr) | 134-136 |

Intermediate A 25: 4-chloro-3-methyl-1-propyl-imidazo[1,5-a]pyrido[3,2-e]pyrazin-8-ol 2 g 4-chloro-8-methoxy-3-methyl-1-propyl-imidazo[1,5-a]pyrido[3,2-e]pyrazine (Intermediate A1) was suspended in 50 ml dichloromethane. At 0-5° C. 3 ml bortribromide was added dropwise, followed by 1 h stirring at 0-5° C., 4 h stirring at room temperature, and standing over night. The reaction mixture was added slowly to a solution of 10 g potassium carbonate in 100 ml water. After stirring and constant pH>7 (adding 10% potassium carbonate solution) the precipitate was filtered off, and washed with water.

Yield: 1.87 g m.p.: 227-234° C. (EtOH)

Other intermediates A of formula (IV) can be prepared according to this procedure. Examples with X=Br were obtained with a period of 6 h heating to reflux. Some examples are the following:

| Intermediate | X | R¹ | R² | R⁴ | m.p. [° C.] |
|---|---|---|---|---|---|
| A25 | —Cl | —C₃H₇ | —CH₃ | —OH | 227-234 |
| A26 | —Br | —C₂H₅ | —CH₃ | —OH | >360° C. (×HBr) |
| A27 | —Br | —C₆H₁₁ | —CH₃ | —OH | 212-216 |

Intermediate A28: 4-chloro-8-difluoromethoxy-3-methyl-1-propyl-imidazo[1,5-a]pyrido[3,2-e]pyrazine 5.51 g (0.02 mol) 4-chloro-3-methyl-1-propyl-9H-imidazo[1,5-a]pyrido[3,2-e]pyrazin-8-ol (Intermediate A25) and 2 g (0.05 mol) sodium hydroxide were dissolved in 20 ml dimethylformamide. After 10 min stirring 2.53 ml (0.03 mol) chlorodifluoroacetic acid was added dropwise. The mixture was heated 5 h at 150° C. bath temperature with stirring. After cooling the product was extracted with ethyl acetate (200 ml, 300 ml), the combined organic phases were washed with water (2×100 ml), the organic phase was dried over sodium sulfate, filtered off, and evaporated to dryness.

The obtained residue with 3 alkylated products was separated by preparative chromatography (silica gel, dichloromethane/methanol=9/1, v/v).

Yield: 1.21 g m.p.: 95-98° C.

Example 1

4,8-dimethoxy-3-methyl-1-propyl-imidazo[1,5-a]pyrido[3,2-e]pyrazine 1.5 g of intermediate A1 are dissolved in a mixture of 15 ml methanol and 15 ml dichloromethane. 1 g of solid KOH is added. The mixture is heated up to reflux for 7 hours. At room temperature 30 ml water are added. The organic layer is separated. The aqueous layer is extracted with 20 ml dichloromethane. The unified organic layers are washed with 2×20 ml water. The solvent is removed completely. The residue is purified by LC.

Yield: 1.2 g m.p.: 112-115° C.

The following examples are prepared using the same route of synthesis and reaction conditions like described above for example 1:

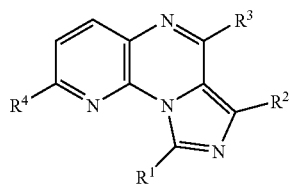

| Example | R¹ | R² | R³ | R⁴ | m.p. [° C.] |
|---|---|---|---|---|---|
| 1 | —C₃H₇ | —CH₃ | —OCH₃ | —OCH₃ | 112-115 |
| 2 | —C₃H₇ | —H | —OCH₃ | —OCH₃ | 113-116 |
| 3 | —C₂H₅ | —CH₃ | —OCH₃ | —OCH₃ | 155-157 |
| 4 | —CH₃ | —CH₃ | —OCH₃ | —OCH₃ | 184-186 |
| 5 | —H | —CH₃ | —OCH₃ | —OCH₃ | 152-154 |
| 6 | —C₂H₅ | —CH₃ | —OCH(CH₃)₂ | —OCH₃ | 80-81 |
| 7 | —C₂H₅ | —CH₃ | —OC₃H₇ | —OCH₃ | 78-81 |
| 8 | —C₂H₅ | —CH₃ | —O-cyclopentyl | —OCH₃ | 76-78 |
| 9 | —C₃H₇ | —CH₃ | —OCH(CH₃)₂ | —OCH₃ | 78-80 |
| 10 | —CH₃ | —CH₃ | —OCH₂-(2,3,6-trifluorophenyl) | —OCH₃ | 227-229 |
| 11 | —C₂H₅ | —CH₃ | —OCH₂-(2,4-dichlorophenyl) | —OCH₃ | 193-195 |
| 12 | —C₂H₅ | —CH₃ | —OCH₂-(2-chloro-6-fluorophenyl) | —OCH₃ | 149-151 |
| 13 | —C₂H₅ | —CH₃ | —OCH₂-(2,3,6-trifluorophenyl) | —OCH₃ | 158-160 |
| 14 | —C₂H₅ | —CH₃ | —OCH₂-(2,4,6-trimethylphenyl) | —OCH₃ | 157-160 |
| 15 | —C₃H₇ | —CH₃ | —OCH₂-(2-chloro-6-fluorophenyl) | —OCH₃ | 163-165 |

-continued

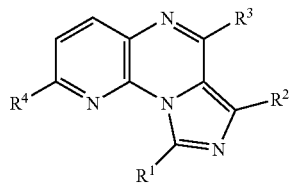

| Example | R¹ | R² | R³ | R⁴ | m.p. [° C.] |
|---|---|---|---|---|---|
| 16 | —C₃H₇ | —CH₃ | —O—CH₂-(2,6-difluorophenyl) | —OCH₃ | 147-149 |
| 17 | —C₂H₅ | —CH₃ | —O—CH₂-phenyl | —OCH₃ | 133-135 |
| 18 | —C₃H₇ | —CH₃ | —O—CH₂-phenyl | —OCH₃ | 129-132 |
| 19 | —CH₃ | —CH₃ | —O—CH₂-phenyl | —OCH₃ | 115-118 |
| 20 | —H | —CH₃ | —O—CH₂-phenyl | —OCH₃ | 111-114 |
| 21 | —C₃H₇ | —CH₃ | —O—CH₂CH₂-phenyl | —OCH₃ | 87-89 |
| 22 | —C₂H₅ | —CH₃ | —O—CH₂CH₂-phenyl | —OCH₃ | 75-78 |
| 23 | —CH₃ | —CH₃ | —O—CH₂CH₂-phenyl | —OCH₃ | 83-85 |
| 24 | —C₂H₅ | —CH₃ | —O—CH₂-(3,5-dimethylisoxazol-4-yl) | —OCH₃ | 173-175 |
| 25 | —C₂H₅ | —CH₃ | —SCH₃ | —OCH₃ | 156-159 |
| 26 | —C₃H₇ | —CH₃ | —SCH₃ | —OCH₃ | 112-115 |
| 27 | —CH₃ | —CH₃ | —SCH₃ | —OCH₃ | 140-144 |
| 28 | —H | —CH₃ | —SCH₃ | —OCH₃ | 185-187 |

Compounds of formula (II) where m and n are 0, the bond between A and N is a double bond and R³ is —CN are preferably prepared by the treatment of an intermediate of formula (IV) with the Grignard reagent ethoxycarbonyl-difluoromethyl magnesium chloride followed by the substitution with a cyanide salt, e.g. KCN.

Example 29

4-cyano-8-methoxy-3-methyl-1-propyl-imidazo[1,5-a]pyrido[3,2e]pyrazine 3 g of intermediate A1 are added into a solution of 32 g ethoxycarbonyl-difluoromethyl magnesia chloride in 100 ml tetrahydrofurane (THF). The mixture is stirred and heated up to reflux for 10 hours. Then the solvent is removed and 15 ml N,N-dimethylformamide and 2 g KCN are added. This reaction mixture is heated up to reflux for 5 hours. After this time 100 ml toluol are added. The organic layer is washed with 3×50 ml water. The solvent is removed and purified by preparative HPLC.

Yield: 0.2 g
m.p.: 178-180° C.

Using the same procedure and reaction conditions like described above for Example 29 also Example 30 was synthesized.

Example 30

4-cyano-8-methoxy-3-methyl-1-ethyl-imidazo[1,5-a]pyrido[3,2-e]pyrazine

Yield: 0.14 g
m.p.: 171-178° C.

Compounds of formula (II) where m and n are 0, the bond between A and N is a double bond and $R^3$ is —$N_3$ are prepared by the treatment of an intermediate of formula (IV) with and an azide salt, e.g. $NaN_3$.

Example 31

4-azido-8-methoxy-3-methyl-1-propyl-imidazo[1,5-a]pyrido[3,2-e]pyrazine 1.5 g of intermediate A1 are stirred into 10 ml N,N-dimethylformamide. 1 g $NaN_3$ is added at room temperature. The mixture is heated up to 60° C. and stirred for 5 hours. 100 ml toluol are added. The organic layer is separated and washed with 3×30 ml water. 90 ml of the solvent are removed. The reaction product precipitates. The crude product is purified by crystallisation from toluol.

Yield: 1.2 g
m.p.: >205° C. (decomp.)

Compounds of formula (II) where m and n are 0, the bond between A and N is a double bond and $R^3$ is $(SO)R^6$ or $(SO_2)R^6$, wherein $R^6$ is as defined above, are prepared by oxidation of the corresponding compounds of formula (II) where $R^3$ means —$SR^6$.

Example 32

8-methoxy-3-methyl-4-methylsulfinyl-1-propyl-imidazo[1,5-a]pyrido[3,2-e]pyrazine and

Example 33

8-methoxy-3-methyl-4-methylsulfonyl-1-propyl-imidazo[1,5-a]pyrido[3,2-e]pyrazine 0.7 g of 8-methoxy-3-methyl-4-methylthio-1-propyl-imidazo[1,5-a]pyrido[3,2-e]pyrazine (Example 26) are dissolved in 40 ml dichloromethane. 0.8 g of 3-chloroperoxybenzoic acid are added at 0 to 5° C. in small portions. The mixture is stirred for 2 hours at room temperature. The solution is washed with 2×30 ml saturated $NaHCO_3$ solution and than with 2×30 ml water. The solvent is removed from the isolated organic layer. The crude mixture of Example 32 and Example 33 is separated by preparative HPLC.

Example 32

Yield: 0.2 g
m.p.: 144-147° C.

Example 33

Yield: 0.25 g
m.p.: 42-46° C.

Example 34 is prepared using the same route of synthesis and reaction conditions like described above for example 31:

Example 34

1-ethyl-8-methoxy-3-methyl-4-methylsulfinyl-imidazo[1,5-a]pyrido[3,2-e]pyrazine

Yield: 0.23 g
m.p.: 189-192° C.

Compounds of formula (II) where m and n are 0, the bond between A and N is a double bond and $R^3$ is hydrogen are preferably prepared by the hydrogenation of an intermediate of formula (IV), e.g. with hydrogen in the presence of a catalyst such as palladium.

Example 35

8-methoxy-3-methyl-1-propyl-imidazo[1,5-a]pyrido[3,2-e]pyrazine 2 g of intermediate A1 are suspended in 50 ml ethanol. 1 ml triethylamine and 1 g palladium catalyst are added. An autoclave is used as reaction vessel. Hydrogen is pressed in up to 20 bar pressure. Now, the mixture is stirred at 30° C. for 4 hours. After filtration the solvent is removed. The crude product is dissolved in 100 ml dichloromethane. This solution is washed with 50 ml water. The solvent is removed to isolate pure product.

Yield: 1.3 g
m.p.: 134-135° C.

Using the same procedure and reaction conditions like described above for Example 35 also Example 36 was synthesized.

Example 36

1-ethyl-8-methoxy-3-methyl-imidazo[1,5-a]pyrido[3,2-e]pyrazine

Yield: 1.0 g
m.p.: 159-162° C.

Compounds of formula (II) where m and n are 0, the bond between A and N is a double bond and $R^3$ is $R^6$ as described above, are preferably prepared by treatment of an intermediate of formula (IV) with the corresponding alkyl-, alkenyl- or alkynyl organometal reagent, e.g. ethyl magnesium bromide.

Example 37

4-ethyl-8-methoxy-3-methyl-1-propyl-imidazo[1,5-a]pyrido[3,2-e]pyrazine 7 g of intermediate A1 are suspended in 150 ml tetrahydrofurane. 30 ml of a solution of ethyl magnesium bromide in tetrahydrofurane (3 M) are added. The mixture is stirred for 4 hours at room temperature. After filtration the solvent is removed. The crude product is purified by preparative HPLC.
Yield: 5.1 g
m.p.: 78-81° C.

The following compounds are prepared using the same route of synthesis and reaction conditions like described above for Example 37:

An analogous compound with $R^3$=$CH_3$ was obtained during the synthesis of the above described of intermediate A28. Separation of the obtained 3 alkylated products by preparative chromatography resulted in Example 59.

Example 59

4-difluoromethoxy-3-methyl-1-propyl-imidazo[1,5-a]pyrido[3,2-e]pyrazine-8-ol Yield: 0.81 g
m.p.: 292-297° C.

Compounds of formula (II) where m is 0, n=1 and the bond between A and N is a double bond are synthesized from

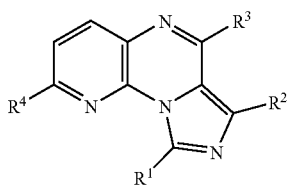

| Example | $R^1$ | $R^2$ | $R^3$ | $R^4$ | m.p. [° C.] |
|---|---|---|---|---|---|
| 37 | —$C_3H_7$ | —$CH_3$ | —$C_2H_5$ | —$OCH_3$ | 78-81 |
| 38 | —$C_3H_7$ | —$CH_3$ | —$CH_3$ | —$OCH_3$ | 91-93 |
| 39 | —$C_3H_7$ | —$CH_3$ | —$CH_3$ | —$OCH_3$ | 171-175 (× HCl) |
| 40 | —$C_2H_5$ | —$CH_3$ | —$CH_3$ | —$OCH_3$ | 106-109 |
| 41 | —$CH_3$ | —$CH_3$ | —$CH_3$ | —$OCH_3$ | 157-161 |
| 42 | —$CH_2CH_2CF_3$ | —$CH_3$ | —$CH_3$ | —$OCH_3$ | 145-147 |
| 43 | —$C_5H_{11}$ | —$CH_3$ | —$CH_3$ | —$OCH_3$ | 70-71 |
| 44 | —$C_6H_{11}$ | —$CH_3$ | —$CH_3$ | —$OCH_3$ | 149-152 |
| 45 | —$C_6H_{13}$ | —$CH_3$ | —$CH_3$ | —$OCH_3$ | 73-75 |
| 46 | —$(CH_2)_2C_6H_5$ | —$CH_3$ | —$CH_3$ | —$OCH_3$ | 121.5-123 |
| 47 | —$C_6H_5$ | —$CH_3$ | —$CH_3$ | —$OCH_3$ | 189-192 |
| 48 | —$C_6H_5$ | —$CH_3$ | —$CH_3$ | —$OCH_3$ | 210-218 (×2 HCl) |
| 49 | —$C_6H_4$(2-Cl) | —$CH_3$ | —$CH_3$ | —$CH_3$ | 220-222 |
| 50 | —$C_6H_4$(4-F) | —$CH_3$ | —$CH_3$ | —$OCH_3$ | 235-238 |
| 51 | —$C_3H_7$ | —$CH_3$ | —$CH_3$ | —$CH_3$ | 104-107 |
| 52 | —$C_3H_7$ | —$CH_3$ | —$CH_3$ | —H | 92-95 |
| 53 | —$C_3H_7$ | H | —$CH_3$ | —$OCH_3$ | 124-126 |
| 54 | —$C_3H_7$ | —$CH_3$ | —$CH_3$ | —$OCHF_2$ | 126-130 |
| 55 | —$C_3H_7$ | —$CH_3$ | —$CH_3$ | —N(piperidinyl) | 98-101 |
| 56 | —$C_2H_5$ | —$CH_3$ | —$CH_3$ | —N(4-methylpiperazinyl) | 146-149 |
| 57 | —$C_2H_5$ | —$CH_3$ | —$CH_3$ | —N(2-Et-4-Me-imidazolyl) | 73-75 |
| 58 | —$C_3H_7$ | —$CH_3$ | —$CH_3$ | —N(2-Pr-4-Me-imidazolyl) | 105-107 | compounds of formula (II) where m and n are 0, the bond between A and N is a double bond by oxidation, e.g. with 3-chloroperoxybenzoic acid.

Example 60

8-methoxy-3-methyl-5-oxo-1-propyl-imidazo[1,5-a]pyrido[3,2-e]pyrazine 6 g of 8-methoxy-3-methyl-1-propyl-imidazo[1,5-a]pyrido[3,2-e]pyrazine (Example 35) are dissolved in 300 ml dichloromethane. A solution of 12 g 3-chloroperoxybenzoic acid in 40 ml acetic acid is added in small portions during 30 minutes. The reaction mixture is stirred for 16 hours at room temperature. Than the solution is washed with 2×50 ml saturated NaHCO$_3$ solution and with 50 ml water. The solvent is removed. The crude product is purified by preparative HPLC.

Yield: 1.5 g
m.p.: 228-232° C.

The same route of synthesis and reaction conditions like described above for Example 37 were used for the synthesis of Example 42.

Example 61

3,4-dimethyl-8-methoxy-5-oxo-1-propyl-imidazo[1,5-a]pyrido[3,2-e]pyrazine

Yield: 1.4 g
m.p.: 154-157° C.

Compounds of formula (II) where m and n are 0, the bond between A and N is a double bond and R$^3$ is NH(CO)OR$^6$, N((CO)OR$^6$)$_2$, N(R$^6$)((CO)OR$^6$), NH(CO)NH$_2$, NH(CO)NHR$^6$, NR$^6$(CO)NH$_2$ and NR$^6$(CO)NHR$^6$ are preferably prepared by treatment of an intermediate of formula (IV) with NH$_3$ or an alkyl amine, e.g. a C$_{1-5}$ alkyl amine to form the corresponding 4-amino derivatives (according to the method from WO 99/45009). These 4-amino derivatives (intermediates B) are treated with suitable reagents such as chloro formic acid esters or amides to prepare the final products.

Intermediate B

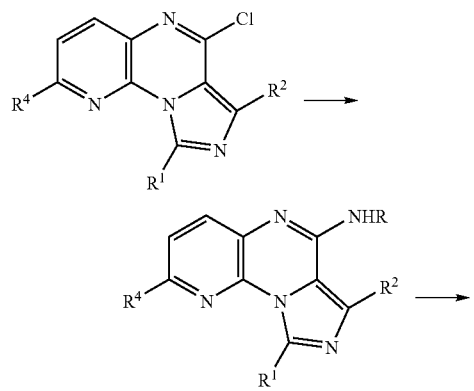

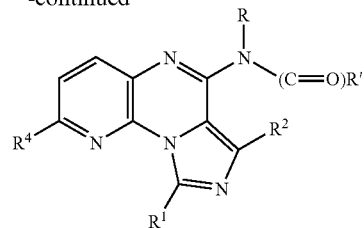

Intermediate B1: 4-amino-8-methoxy-3-methyl-1-propyl-imidazo[1,5-a]pyrido[3,2-e]pyrazine 10 g of intermediate A1 and 200 ml of an aqueous solution of NH$_3$ (32%) are mixed in an autoclave and heated up to 130° C. for 8 hours. The reaction mixture is diluted with 200 ml water. The precipitated reaction product is separated washed with water and dichloro methane and dried at reduced pressure.

Yield: 8.5 g
m.p.: 219-221° C.

Example 62

8-methoxy-4-methoxycarbonylamino-3-methyl-1-propyl-imidazo[1,5-a]pyrido[3,2-e]pyrazine 1.4 g of the intermediate B1 are stirred with 20 ml dichloromethane 5 ml methanol and 1 ml triethylamine. At 0° C. a solution of 0.6 g chloro formic acid methylester in 10 ml dichloromethane is added slowly. The mixture is stirred for 2 hours at 0° C. Than the solution is heated up to reflux 10 hours. The solution is washed with 30 ml saturated NaHCO$_3$ solution and with 30 ml water. The solvent is removed. The crude product is purified by preparative HPLC.

Yield: 0.22 g
m.p.: 137-138° C.

Further Examples prepared using the same route of synthesis and reaction conditions like described above for Example 62 are the following:

Example 63

4-ethoxycarbonylamino-8-methoxy-3-methyl-1-propyl-imidazo[1,5-a]pyrido[3,2-e]pyrazine Yield: 0.3 g
m.p.: 122-124° C.

Example 64

4-(N,N-bis-methoxycarbonyl-)amino-8-methoxy-3-methyl-1-propyl-imidazo[1,5-a]pyrido[3,2-e]pyrazine Yield: 0.45 g
m.p.: 137-138° C.

Example 65

8-methoxy-4-(methoxycarbonyl-methyl-amino)-3-methyl-1-propyl-imidazo[1,5-a]pyrido[3,2-e]pyrazine Yield: 0.04 g
m.p.: 105-109° C.

Example 66

8-methoxy-3-methyl-4-(3-methyl-ureido)-1-propyl-imidazo[1,5-a]pyrido[3,2-e]pyrazine 543 mg of Intermediate B1 and 960 mg N,N'-carbonyldiimidazole were stirred with 20 ml tetrahydrofurane for 3 hours under reflux. At room temperature 3 ml 40% methylamine solution was added slowly. The solution was heated up to reflux 30 minutes. After removing the solvent under reduced pressure the residue was extracted with 50 ml dichloromethane and 2×25 ml water. The organic layer is removed. The crude product was purified by preparative HPLC.

Yield: 0.4 g
m.p.: 178-181° C.

Further Examples prepared using the same route of synthesis and reaction conditions like described above for Example 66 are the following:

Example 67

8-methoxy-3-methyl-1-propyl-4-ureido-imidazo[1,5-a]pyrido[3,2-e]pyrazine

Yield: 0.5 g
m.p.: 185-187° C.

Example 68

8-methoxy-3-methyl-4-(3-isopropyl-ureido)-1-propyl-imidazo[1,5-a]pyrido[3,2-e]pyrazine Yield: 0.3 g
m.p.: 165-166° C.

Compounds of formula (II) where m and n are 0, the bond between A and N is a double bond and $R^3$ is $NH-SO_2R^6$, $N(SO_2R^6)_2$, $N(R^6)(SO_2R^6)$, $NHSO_2R^7$, $N(SO_2R^7)_2$ and $N(R^8)SO_2R^7$, wherein $R^6$, $R^7$ and $R^8$ are as defined above, are preferably prepared by treatment of an intermediate of formula (IV) with $NH_3$ or an alkyl amine, e.g. a $C_{1-5}$ alkyl amine to form the corresponding 4-amino derivatives according to the method from WO 99/45009. These 4-amino derivatives (intermediates B) are treated with sulfonic acid chlorides or anhydrides forming the final sulfonamides.

Example 69

8-methoxy-3-methyl-4-methylsulfonylamino-1-propyl-imidazo[1,5-a]pyrido[3,2-e]pyrazine 10 g of the intermediate B1 are mixed with 350 ml toluol and 14 g methylsulfonic acid anhydride. The mixture is heated up to reflux for 1 hour. After this time 16 ml triethylamine are added at 70° C. The mixture is stirred then for 1 hour. 100 ml water are added. The product precipitates. After filtration it is washed with 3×80 ml water and 3×80 ml toluol. The product is crystallized from toluol.

Yield: 9 g
m.p.: 243-246° C.

Further Examples prepared using the same route of synthesis and reaction conditions like described above for Example 46 are the following:

| Example | $R^1$ | $R^2$ | $R^3$ | $R^4$ | m.p. [° C.] |
|---|---|---|---|---|---|
| 69 | $-C_3H_7$ | $-CH_3$ | $-NHSO_2CH_3$ | $-OCH_3$ | 243-246 |
| 70 | $-C_3H_7$ | $-CH_3$ | $-N(SO_2CH_3)_2$ | $-OCH_3$ | 198-200 |
| 71 | $-C_3H_7$ | $-CH_3$ | $-NHSO_2C_2H_5$ | $-OCH_3$ | 189-190 |
| 72 | $-C_2H_5$ | $-CH_3$ | $-NHSO_2CH_3$ | $-OCH_3$ | 270-271 |
| 73 | $-C_3H_7$ | $-CH_3$ | $-NHSO_2CF_3$ | $-OCH_3$ | 213-216 |
| 74 | $-C_3H_7$ | $-CH_3$ | $-NHSO_2C_3H_7$ | $-OCH_3$ | 203-206 |
| 75 | $-C_3H_7$ | $-CH_3$ | $-NHSO_2CH(CH_3)_2$ | $-OCH_3$ | 235-238 |
| 76 | $-C_3H_7$ | $-CH_3$ | $-NHSO_2(C_6H_4\text{-}4\text{-}CH_3)$ | $-OCH_3$ | 229-232 |
| 77 | $-C_3H_7$ | $-CH_3$ | $-N[SO_2(C_6H_4\text{-}4\text{-}CH_3)]_2$ | $-OCH_3$ | 206-209 |
| 78 | $-(CH_2)_2CF_3$ | $-CH_3$ | $-NHSO_2CH_3$ | $-OCH_3$ | 250-253 |
| 79 | $-C_6H_{13}$ | $-CH_3$ | $-NHSO_2CH_3$ | $-OCH_3$ | 134-136 |
| 80 | $-(CH_2)_2C_6H_5$ | $-CH_3$ | $-NHSO_2CH_3$ | $-OCH_3$ | 199-202 |
| 81 | $-C_6H_5$ | $-CH_3$ | $-NHSO_2CH_3$ | $-OCH_3$ | 217-220 |
| 82 | $-C_6H_4(2\text{-}Cl)$ | $-CH_3$ | $-NHSO_2CH_3$ | $-OCH_3$ | 246-251 |
| 83 | $-C_6H_4(4\text{-}F)$ | $-CH_3$ | $-NHSO_2CH_3$ | $-OCH_3$ | 250-256 |
| 84 | $-C_3H_7$ | $-CH_3$ | $-NHSO_2CH_3$ | (2-Pr-4-Me-imidazolyl) | 224-225 |

Example 85

3-methyl-4-methylsulfonylamino-1-propyl-imidazo[1,5-a]pyrido[3,2-e]pyrazin-8-ol hydrobromide 3 g 8-methoxy-3-methyl-4-methylsulfonylamino-1-propyl-imidazo[1,5-a]pyrido[3,2-e]pyrazine (Example 69) was suspended in 150 ml dichloromethane. At 0-5° C. 3.3 g bortribromide was added dropwise, followed by 30 min stirring at 0-5° C., 30 min stirring at room temperature, and 2 h at 30° C. The reaction mixture was added slowly to a solution of 10 g sodium carbonate in 100 ml water. After stirring and constant pH>7 (adding 10% potassium carbonate solution) the precipitate was filtered off, washed with water, dried, and recrystallized with ethanol.

Yield: 0.5 g
m.p.: 302-306° C.

Example 86

3-methyl-4-methylsulfonylamino-1-propyl-imidazo[1,5-a]pyrido[3,2-e]pyrazin-8-ol

Example 86 can be prepared according to procedure of Example 85 without 2 h stirring at 30° C.

Yield: 0.5 g
m.p.: 295-297° C.

Example 87

8-difluoromethoxy-3-methyl-4-methylsulfonylamino-1-propyl-imidazo[1,5-a]pyrido[3,2-e]pyrazine 4.98 g 3-methyl-4-methylsulfonylamino-1-propyl-imidazo[1,5-a]pyrido[3,2-e]pyrazin-8-ol (Example 86) and 1.6 g sodium hydroxide were dissolved in 20 ml dimethylformamide. After 10 min stirring 1.85 ml chlorodifluoroacetic acid was added dropwise. The mixture was heated 5 h at 150° C. bath temperature with stirring. After cooling the product was extracted with ethyl acetate (200 ml, 300 ml), the combined organic phases were washed with water (2×100 ml), the organic phase was dried over sodium sulfate, filtered off, and evaporated to dryness.

The obtained residue was separated by preparative chromatography (silica gel, dichloromethane/methanol=9/1, v/v).

Yield: 0.66 g
m.p.: 210-214° C.

Example 88

8-cyclopropylmethoxy-3-methyl-4-methyl sulfonylamino-1-propyl-imidazo[1,5-a]pyrido[3,2-e]pyrazine 0.83 g 3-methyl-4-methylsulfonylamino-1-propyl-imidazo[1,5-a]pyrido[3,2-e]pyrazin-8-ol (Example 86) was dissolved in 20 ml dimethylformamide. 1.14 g cesium carbonate was added followed by 0.44 ml cyclopropyl bromide dropwise. The mixture was heated 1 h at 60° C. and 3 h at 130° C. bath temperature with stirring. After cooling the product was extracted with ethyl acetate (2×50 ml), and water (2×50 ml), the organic phase was dried over sodium sulfate, filtered off, and evaporated to dryness.

The obtained residue was separated by preparative chromatography (silica gel, dichloromethane/methanol=95/5, v/v).

Yield: 0.26 g
m.p.: 212-216° C.

Compounds of formula (II) where m=1, n is 0, the bond between A and N is a single bond and $R^5$ is hydrogen are prepared by the reduction of an intermediate of formula (IV) with hydrogen, e.g. in the presence of a catalyst such as palladium.

Example 89

3-methyl-1-propyl-4,5-dihydro-imidazo[1,5-a]pyrido[3,2-e]pyrazine 6 g of the intermediate A12 are suspended in 200 ml ethanol. 3 ml triethylamine and 3 g palladium catalyst are added. An autoclave is used as reaction vessel. Hydrogen is pressed in up to 20 bar pressure. Now, the mixture is stirred at 70° C. for 4 hours. After filtration the solvent is removed. The crude product is dissolved in 100 ml dichloromethane. This solution is washed with 50 ml water. The solvent is removed to isolate the pure product.

Yield: 4.5 g
m.p.: 169-172° C.

Further Examples prepared using the same route of synthesis and reaction conditions like described above for Example 89 are the following:

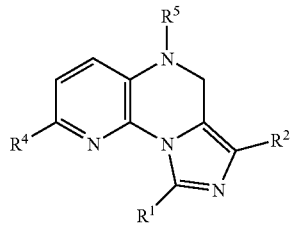

| Example | $R^1$ | $R^2$ | $R^4$ | $R^5$ | m.p. [° C.] |
|---|---|---|---|---|---|
| 89 | —$C_3H_7$ | —$CH_3$ | —H | —H | 169-172 |
| 90 | —$C_3H_7$ | —H | —$OCH_3$ | —H | 45-49 |
| 91 | —$C_3H_7$ | —$CH_3$ | —$OCH_3$ | —H | 157-160 |
| 92 | —$C_3H_7$ | —$CH_3$ | —$OCH_3$ | —H × HCl | 228-231 |
| 93 | —$C_2H_5$ | —$CH_3$ | —$OCH_3$ | —H | 139-142 |

Compounds of formula (II) where m=1, n is 0, the bond between A and N is a single bond and $R^5$ is —$C_{1-5}$ alkyl are prepared by the treatment of compounds of formula (II) where m=1, n is 0, the bond between A and N is a single bond and $R^5$ is hydrogen with a $C_{1-5}$alkyl-aldehyde, e.g. in the presence of Raney-Nickel and hydrogen.

Example 94

3,5-dimethyl-8-methoxy-1-propyl-4,5-dihydro-imidazo[1,5-a]pyrido[3,2-e]pyrazine 1 g 8-methoxy-3-methyl-1-propyl-4,5-dihydro-imidazo[1,5-a]pyrido[3,2-e]pyrazine (Example 91) is suspended in 70 ml methanol. 1 ml methanal and 0.5 g Raney-Nickel are added. An autoclave is used as reaction vessel. Hydrogen is pressed in up to 20 bar pressure. Now, the mixture is stirred at 45° C. for 8 hours. After filtration the solvent is distilled off.

Yield: 0.97 g
m.p.: 113-116° C.

Compounds of formula (II) where m=1, n is 0, the bond between A and N is a single bond and $R^5$ is —(C=O)—$C_{1-5}$ alkyl are prepared by treatment of compounds of formula (II) where m=1, n is 0, the bond between A and N is a single bond and $R^5$ is hydrogen with alkyl acid chlorides or anhydrides.

Example 95

5-acetyl-8-methoxy-3-methyl-1-propyl-4,5-dihydro-imidazo[1,5-a]pyrido[3,2-e]pyrazine 1 g 8-methoxy-3-methyl-1-propyl-4,5-dihydro-imidazo[1,5-a]pyrido[3,2-e]pyrazine (Example 91) is suspended in 25 ml dichloromethane. 0.8 g triethylamine are added. At 0° C. a solution of 0.4 g acetyl chloride in 5 ml dichloromethane is added. The mixture is stirred for 2 hours at room temperature. 25 ml water are added. The organic layer is separated. The solvent is distilled off.

Yield: 1 g
m.p.: 114-116° C.

The Synthesis of the preferred compound (Example 38/39) is described in the following scheme over all steps:

Step 1: 6-methoxy-2-(4-methyl-2-propyl-imidazol-1-yl)-3-nitro-pyridine

To a suspension prepared of 20.0 g KOH (solid), 25.8 g 4-methyl-2-propyl imidazole and 130 ml dimethyl formamide were added 38.0 g 2-chloro-6-methoxy-3-nitro pyridine in small amounts at a reaction temperature of 5° C. The reaction mixture was stirred for 75 minutes at room temperature. Then the reaction mixture was poured in 600 ml water. The mixture was further stirred for 1 hr. The desired product precipitated during this time. The resulting solid was collected by filtration, washed with 100 ml water for 3 times and dried in a dry box with vacuum (40° C.).

Yield: 40 g
m.p.: 96-103° C.

Step 2: 3-amino-6-methoxy-2-(4-methyl-2-propyl-imidazol-1-yl)-pyridine

To a solution prepared of 138.2 g 6-methoxy-2-(4-methyl-2-propyl-imidazol-1-yl)-3-nitro-pyridine and 900 ml ethyl alcohol 4 g palladium-charcoal were added. The reaction mixture was heated to 40° C. and then hydrogenated under pressure (10 to 15 bar). At room temperature the catalyst was filtrated off and the filtrate was evaporated. To the solid residue 150 ml methyl tert.-butyl ether (MTBE) were added. After stirring for 30 minutes the product was collected by filtration, washed with 50 ml MTBE for 2 times and dried in a dry box with vacuum (40° C.).

Yield: 100 g
m.p.: 124-128° C.

Step 3: 8-methoxy-3-methyl-1-propyl-imidazo[1,5-a]-pyrido[3,2-e]-pyrazinone

A mixture of 20 g 3-amino-6-methoxy-2-(4-methyl-2-propyl-imidazol-1-yl)-pyridine and 60 g urea were heated up to 160° C. The reaction mixture was stirred for 2 hrs. Then 10 ml of glacial acetic acid were added. The stirring was continued for further 6 hrs. The reaction mixture was allowed to cool. At a temperature of 70° C. 300 ml of water were added and the mixture was stirred for 1 hr at 50° C. The warm mixture was filtrated and washed with 50 ml of water for 2 times and dried in a dry box.

Yield: 20.5 g
m.p.: 297-300° C.

Step 4: 4-chloro-8-methoxy-3-methyl-1-propyl-imidazo[1,5-a]-pyrido[3,2-e]-pyrazine A mixture of 27 g 8-methoxy-3-methyl-1-propyl-imidazo[1,5-a]-pyrido[3,2-e]-pyrazinone and 225 ml phosphorus oxychloride were heated to reflux for 8 hrs. To the cooled mixture 250 ml of toluene were added and then 350 ml of the liquid were distilled off. Subsequently the same procedure was performed with 150 ml toluene but 250 ml of the liquid were distilled off. The reaction mixture was allowed to cool at room temperature and then poured in a mixture of 500 g ice/500 ml water. After 30 minutes the mixture was extracted with 250 ml of dichloromethane for two times. The dichloromethane layer was then washed with 500 ml water then with sodium carbonate (3% in water) and after that with 500 ml water. The organic layer was dried with sodium sulfate. After removal of the sodium sulfate and evaporation of the dichloromethane the crude product was dried in a dry box with vacuum (40° C.).

Yield: 26.5 g
m.p.: 119-123° C.

Step 5: 3,4-Dimethyl-8-methoxy-1-propyl-imidazo[1,5-a]-pyrido[3,2-e]-pyrazine (Example 38)

To a solution prepared of 20 g 4-chloro-8-methoxy-3-methyl-1-propyl-imidazo[1,5-a]-pyrido[3,2-e]-pyrazine (Intermediate 3) and 400 ml tetrahydrofuran 80 ml methylmagnesium bromide (3 M in diethyl ether) were added drop wise (via 2 hrs). The reaction mixture was stirred at room temperature for 6 hours. After that the mixture was poured in a mixture of 300 g water, which contained 100 g of ice and 10 g of ammonium chloride. The mixture was extracted for 4 times with 300 ml dichloromethane. The organic layer was separated and then dried with sodium sulfate. After removal of the sodium sulfate and evaporation of the dichloromethane a yellowish-orange crude product remained. This residue was stirred in 150 ml of diethyl ether. After 1 hr. the product was filtrated off and dried in a dry box.

The yield was 11.9 g of crude product (content >95%).

To a solution of 0.05 mol of the crude product and 100 ml of dichloromethane 2.5 equiv. of hydrochloric acid dissolved in 100 ml of water were added. The mixture was vigorously stirred. The dichloromethane layer was then separated and subsequently the water layer was extracted for 6 times with 100 ml dichloromethane. To the organic layer 15 g of sodium carbonate were added. After filtration of the solid precipitate and evaporation of the dichloromethane yellowish crystals remains.

Yield: 18.6 g
m.p.: 91-92.5° C.

Step 6: 3,4-Dimethyl-8-methoxy-1-propyl-imidazo[1,5-a]-pyrido[3,2-e]-pyrazine hydrochloride (Example 39)

To a solution of 13.52 g of pure 3,4-dimethyl-8-methoxy-1-propyl-imidazo-[1,5-a]-pyrido[3,2-e]-pyrazine and 100 ml of dichloromethane 2.5 equivalents of hydrochloric acid dissolved in 100 ml of water were added. The mixture was vigorously stirred. The dichloromethane layer was then separated and subsequently the water layer was extracted for 6 times with 100 ml dichloromethane. After evaporation of the dichloromethane yellowish crystals remains. (yield 85%; yellowish crystals; m.p. 171-175° C.).

Yield: 13.05 g m.p.: 171-175° C.

Surprisingly, the compounds of formula (II) are potent inhibitors of the enzyme PDE10. A substance is considered to effectively inhibit PDE10 if it has an $IC_{50}$ of less than 10 µM, preferably less than 1 µM.

Preparation and Characterization of PDE10

Phosphodiesterase isoenzyme 10 (PDE10) activity was determined in preparations of rat, pig and guinea pig striatum respectively. Striatum from male Wistar rats (180-200 g), male hybrid pigs (150 kg) and male guinea pigs (CRL (HA), 500 g) respectively were collected and frozen at −70° C.

In the prepared brain areas gene segments containing the catalytic domain of the PDE10 were amplified and the sequence determined. Therefore the RNA from the frozen striatum of the different animals was isolated according to the instructions of the RNeasy kit (Qiagen; Hilden; Germany) and transcribed into cDNA using Oligo-Primer provided with the 1$^{st}$ strand cDNA synthese kit for RT-PCR (Roche; Mannheim; Germany). These cDNA was used as template for the PCR-reaction to amplify the catalytic domain of the PDE10. For the PCR reaction Taq-Polymerase (Promega; Mannheim; Germany) was used. Therefore it was possible to clone the amplificates directly by TA-cloning in the pCR2.1 vector (Invitrogen; Karlsruhe; Germany). The cloning vector was transformed into *E. coli*'s (XL-2), replicated within the cells, prepared and the included gene sequence determined for the pig and the guinea pig.

The following primers were used for the PCR-reaction:

```
P1:  tgcatctacagggttaccatggagaa         (SEQ ID NO:1)

P2:  tatccctgcaggccttcagcagaggctct      (SEQ ID NO:2)

P3:  ttcacatggatatgcgacggtaccttct       (SEQ ID NO:3)

P4:  Ctgtgaagaagaactatcggcgggttcctta.   (SEQ ID NO:4)
```

For the pig the priming was successful with P1 and P2. The following sequence (SEQ ID NO 5) was identified:

```
tgcatctacagggttaccatggagaagctgtcctaccacagcatttgtac cgcggaagagtggcaaggcctcatgcgcttcaaccttcccgtccgtctttt gcaaggagattgaattgttccacttcgacattggtccttttgaaaacatg tggcctggaatctttgtctatatggttcatcgcttctgtgggacggcctg ctttgagcttgaaaagctgtgtcgttttatcatgtctgtgaagaagaact atcgtcgggttccttaccacaactggaagcacgcggtcacggtggcacac tgcatgtacgccatcctccagaacagccacgggctcttcaccgacctcga gcgcaaaggactgctaatcgcgtgtctgtgccacgacctggaccacaggg gcttcagcaacagctacctgcagaaattcgaccaccccctggccgctctc tactccacgccaccatggagcagcaccacttctcccagaccgtgtccat cctccagttggaagggcacaacatcttctccaccctgagctccagtgagt acgagcaggtgcttgagatcatccgcaaagccatcattgccacagacctc gctttgtactttggaaacaggaaacagttggaggagatgtaccagaccgg atcgctaaaccttaataaccagtcacatagagaccgcgtcattggtttga
``` tgatgactgcctgtgatctctgttccgtgacaaaactgtggccagtaaca aaactgacggcaaatgatatatatgcggaattctgggccgagggcgatga ggtgaagaagctgggaatacagcctattcccatgatggacagagacaaga aggacgaagtcccacaaggccagctcggattctacaacgcggtagctatc ccctgctacaccaccctcacccagatcttcccgcccacagagcctcttct gaaggcctgcagggata For the guinea pig the priming was successful with P4 and P2 as well as for P2 and P3.

The following sequence (SEQ ID NO: 6) was identified with P4 and P2:

```
ctgtgaagaagaactatcggcgggttccttaccacaactggaagcatgca gtcacggtggcgcactgcatgtacgccatacttcaaaacaacaatggcct cttcacagaccttgagcgcaaaggcctgctaattgcctgtctgtgccatg acctggaccacaggggcttcagtaacagctacctgcagaaattcgaccac cccctggctgcgttgtactccacctccaccatggagcaacaccacttctc ccagacggtgttcatcctccagctggaaggacacaacatcttctccaccc tgagctccagcgagtacgagcaggtgctggagatcatccgcaaagccatc atcgccactgacctcgcactgtactttgggaacaggaagcagttggagga gatgtaccagacagggtcgctgaacctcaataaccagtcccatcgagacc gcgtcatcggcttgatgatgactgcctgcgatctttgctctgtgacgaaa ctatggccagttacaaaattgacagcaaatgatatatatgcagagttctg ggctgaggggggatgagatgaagaagttggggatacagcccatccctatga tggacagagacaagaaggatgaagtccctcaaggacagcttggattctac aatgctgtggccatcccctgctataccaccctgacgcagatcctcccacc cacagagcctctgctgaaggcctgcagggata
```

The following sequence (SEQ ID NO: 7) was identified with P2 and P3:

```
tagagcctctgctgaaggcctgcagggataacctcaatcagtgggagaag gtaattcgaggggaagagacagcaatgtggatttcaggcccagcaactag caaaagcacatcagggaagccgaccaggaaggtcgatgactgatcctgag gtgatgtctgcctagcaactgactcaacctgcttctgtgacttcgttctt tttattttttatttttttaacggggtgaaaacctctctcagaaggtaccgt cgcatatccatgtgaa
```

An alignment of the sequences showed a nearly complete accordance between the rat (published gene-number-NM_ 022236 3437 bp; coding sequence: 281-2665; catalytic domain 1634-2665) and the guinea pig. More differences were detect between rat and pig. For the alignment the coding areas are used only. The gene alignment is shown in FIG. 3.

This results in the following differences in the protein sequences within the catalytic domain as shown in a protein alignment (FIG. 4).

For the enzymatic testing of PDE10 activity 0.5 g of the isolated and frozen striatum was homogenised in 10 ml 50 mM Tris/Mg-buffer at 4° C. and centrifuged for one hour at 100000 g. The supernatant is called the cytosolic fraction and was removed and stored on ice. The pellet was resuspended in the same buffer, but containing 1% Triton and incubated for 45 min at 4° C. Both fractions were independently applied onto a 5 ml-Hi Trap™ QHP column at the Äkta-FPLC. After washing the columns the bound PDE protein was eluted with an increasing sodium chloride gradient (0 mM-500 mM sodium chloride) in 50 mM Tris/Mg-buffer at 4° C. for the cytosolic fraction and in the presence of 1% Triton for the membrane fraction. The eluted and collected fractions were tested with 100 nM [$^3$H]-cAMP for PDE10-activity in the presence and without a specific PDE-Inhibitor at a concentration, were a 100% inhibition is expected. The fractions with PDE10-activity were pooled and frozen in aliquots until use at −20° C.

The pooled fractions from the FPLC were additional characterized by Western blot. It was shown, that the PDE10A containing pooled fractions include a great number of other cellular proteins. Nevertheless PDE10 was detected with specific antibodies by Western blot clearly (FIG. 1).

The protein was proven in the preparation of the striatum of the rat, the pig and the guinea pig. The main part of protein was found in the membrane fraction (FIG. 2).

Inhibition of PDE10

PDE10 activity was determined in a one step procedure in microtiterplates. The reaction mixture of 100 µl contained 50 mM Tris-HCl/5 mM $MgCl_2$ buffer (pH=7.4) (Sigma, Deisenhofen. Germany; Merck, Darmstadt, Germany) 0.1 µM [$^3$H]-cAMP (Amersham, Buckinghamshire, UK) and the enzyme. Nonspecific activity was tested without the enzyme. The reaction was initiated by addition of the substrate solution and was carried out at 37° C. for 30 minutes. Enzymatic activity was stopped by addition of 25 µl YSi-SPA-beads (Amersham-Pharmacia). One hour later the mixture was measured in a liquid scintillation counter for microtiterplates (Microbeta Trilux). To pipette the incubation mixture a robot Biomek (Fa. Beckman) is used. The determined Km-values for the substrate cAMP is 78 nM for PDE10 from rat striatum, 88 nM for pig striatum and 66.7 nM for guinea pig striatum respectively. cGMP is the second substrate for PDE10, the Km values are 1800 nM, 2200 nM and 1700 nM for PDE10 from these species. For the test with cGMP 500 nM of this substrate was used. The optimal amount of enzyme in the assay has been determined and optimised for each enzyme preparation and substrate separately before using the enzyme in compound testing. For determination of $IC_{50}$ values the Hill-plot, 2-parameter-model, was used. Specific inhibitors of other PDE-Subtypes do not inhibit the PDE10 preparation significantly. Papaverine was used as the most common PDE10 inhibitor and inhibits the PDE10 with IC50 values of 142 nM, 110 nM and 77 nM for PDE10 from striatum of rat, pig and guinea pig respectively.

| Example | Inhibition of PDE10 from rat $IC_{50}$ [µM] |
|---|---|
| 35 | 0.061 |
| 38 | 0.012 |
| 62 | 0.035 |
| 63 | 0.563 |
| 69 | 0.011 |
| 70 | 0.072 |
| 91 | 0.159 |
| 95 | 0.335 |

| Example | Inhibition of PDE10 from pig $IC_{50}$ [µM] |
|---|---|
| 1 | 0.010 |
| 29 | 0.013 |
| 30 | 0.020 |
| 31 | 0.171 |
| 35 | 0.040 |
| 38 | 0.006 |
| 39 | 0.005 |
| 40 | 0.024 |
| 41 | 0.118 |
| 42 | 0.059 |
| 43 | 0.035 |
| 44 | 0.003 |
| 45 | 0.053 |
| 46 | 0.049 |
| 47 | 0.006 |
| 48 | 0.007 |
| 49 | 0.001 |
| 52 | 0.053 |
| 53 | 0.043 |
| 54 | 0.018 |
| 55 | 0.014 |
| 57 | 0.011 |
| 58 | 0.002 |
| 59 | 0.011 |
| 60 | 0.023 |
| 62 | 0.006 |
| 63 | 0.189 |
| 65 | 0.559 |
| 66 | 0.752 |
| 67 | 0.083 |
| 68 | 0.141 |
| 69 | 0.005 |
| 71 | 0.126 |
| 72 | 0.088 |
| 73 | 0.019 |
| 75 | 0.078 |
| 79 | 0.011 |
| 80 | 0.037 |
| 84 | 0.025 |
| 85 | 0.013 |
| 86 | 0.023 |
| 87 | 0.015 |
| 91 | 0.108 |
| 95 | 0.222 |

| Example | Inhibition of PDE10 from guinea pig $IC_{50}$ [µM] |
|---|---|
| 29 | 0.018 |
| 30 | 0.051 |
| 38 | 0.019 |
| 47 | 0.015 |
| 58 | 0.004 |
| 62 | 0.026 |
| 69 | 0.011 |

The compounds of formula II show significant-antipsychotic effects on the MK-801-induced hyperactivity and stereotyped sniffing, an animal model of psychosis.

Test Procedure:

Female Wistar rats (Crl: (WI) BR, Charles River, Sulzfeld, Germany) weighing 150 to 180 g were used for the MK-801-induced psychosis. Animals were housed under standard conditions in groups of five on a 12 h light/dark cycle (light on at 0600 h) with ad libitum access to food (Pellets, ssniff M/R 15, Spezialdiät GmbH, Soest/Westfalen) and MK-801 (dizocilpine, MW 337.37) was obtained by Tocris, distributed by Biotrend Chemikalien GmbH, Köln, Germany.

Drug administration schedule/dosage:

| Substance | dosage [mg/kg] | pre-treatment [min] | number of application [n] | route of administration |
|---|---|---|---|---|
| MK-801 | 0.1 | 10 | 1 | i.p. |
| Example 91 | 15, 30 | 30 | 1 | i.p. |
| Example 35 | 10, 30 | 30 | 1 | p.o. |
| Example 95 | 10, 30 | 30 | 1 | p.o. |
| Example 62 | 2.5, 5.0 | 30 | 1 | p.o. |
| Example 38 | 1.0, 2.5, 5.0 | 30 | 1 | p.o. |
| Example 69 | 1.0, 2.5, 5.0 | 30 | 1 | p.o. |
| Example 29 | 2.5, 5.0, 7.5, 10 | 30 | 1 | p.o. |
| Example 47 | 5.0, 7.5, 10 | 30 | 1 | p.o. |
| Example 30 | 5.0, 10, 15, 20 | 60 | 1 | p.o. |
| Example 55 | 10, 30 | 30 | 1 | p.o. |

Preparation of Compounds:

Compounds were freshly suspended in 0.5% hydroxyethylcellulose so that an administration volume of 0.5 ml/100 g was reached for each substance and dose. Hydroxyethylcellulose was solved in distilled water.

MK-801 was solved in saline so that an administration volume of 0.5 ml/100 g was reached. The suspensions and solution were placed on a magnetic stirrer before and during dosing procedures.

The behaviour induced by the NMDA antagonist MK-801 is generally accepted as a rat model of psychosis. MK-801 induces stereotyped sniffing, hyperactivity and ataxia in rats after intraperitoneal administration.

Locomotor activity of the rats was recorded by the MotiTest Apparatus (TSE, Bad Homburg, Germany). The test area consisted of a squared arena (45×45 cm) with protective plexiglass walls (20 cm of height) where rats could freely move. Horizontal movements were recorded by 32 infrared photocells arranged along the bottom of each wall of the arena. The activity [sec] was measured by the computer program "ActiMot" (TSE, Bad Homburg, Germany).

Stereotyped sniffing was scored by the experimenter every five minutes for one hour (12 intervals) according to the method described by Andiné et al. (1999). The scores of the 12 intervals were summed up at the end of the recording time.

| score | stereotyped sniffing |
|---|---|
| 0 | no stereotyped sniffing |
| 1 | discontinuous sniffing (free interval > 5 s) |
| 2 | continuous sniffing |

The day of experiment the female rats were placed in the laboratory and received the test compound or vehicle at the appropriate time prior to test. MK-801 0.1 mg/kg was intraperitoneally administered 10 minutes prior to test.

At the beginning of the test the rats were placed in the centre of the squared arena of the MotiTest apparatus. Behaviour of the rats was recorded for one hour. After each run animals were removed and the boxes thoroughly cleaned and dried.

Statistics:

Results were analysed by one way analysis of variance (ANOVA). Tukey test was used for individual comparison. $P<0.05$ was regarded as significant.

Results:

The results are shown in FIGS. 5, 6, 7 and 8.

Figure 5:
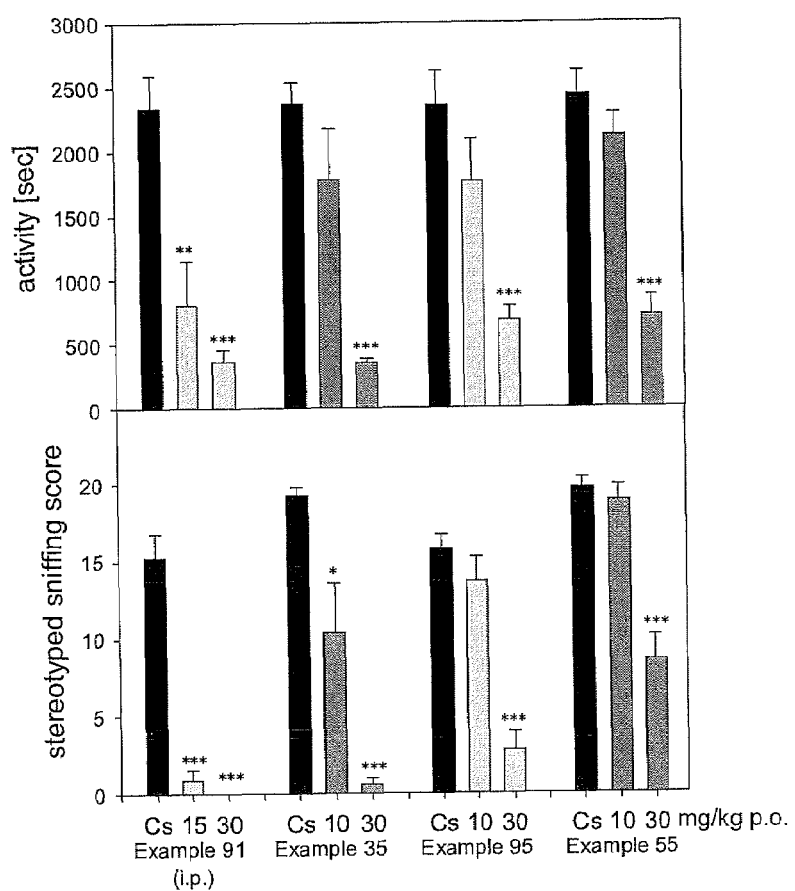
FIG. 5 shows the effect of the compounds of Examples 91, 35, 95 and 55 on MK-801-induced psychosis.

FIG. 5 shows the effect of the compounds of Example 91, 35, 95 and 55 on MK-801-induced psychosis MK-801 at 0.1 mg/kg i.p. was administered 10 min before testing. Compounds at the described doses were administered 30 min prior to the test. Activity and stereotyped sniffing was recorded for 1 h. Cs=control with MK-801 stimulation. Significant to MK-801 stimulated control (=Cs): * $p<0.05$, *** $p<0.001$.

Figure 6:
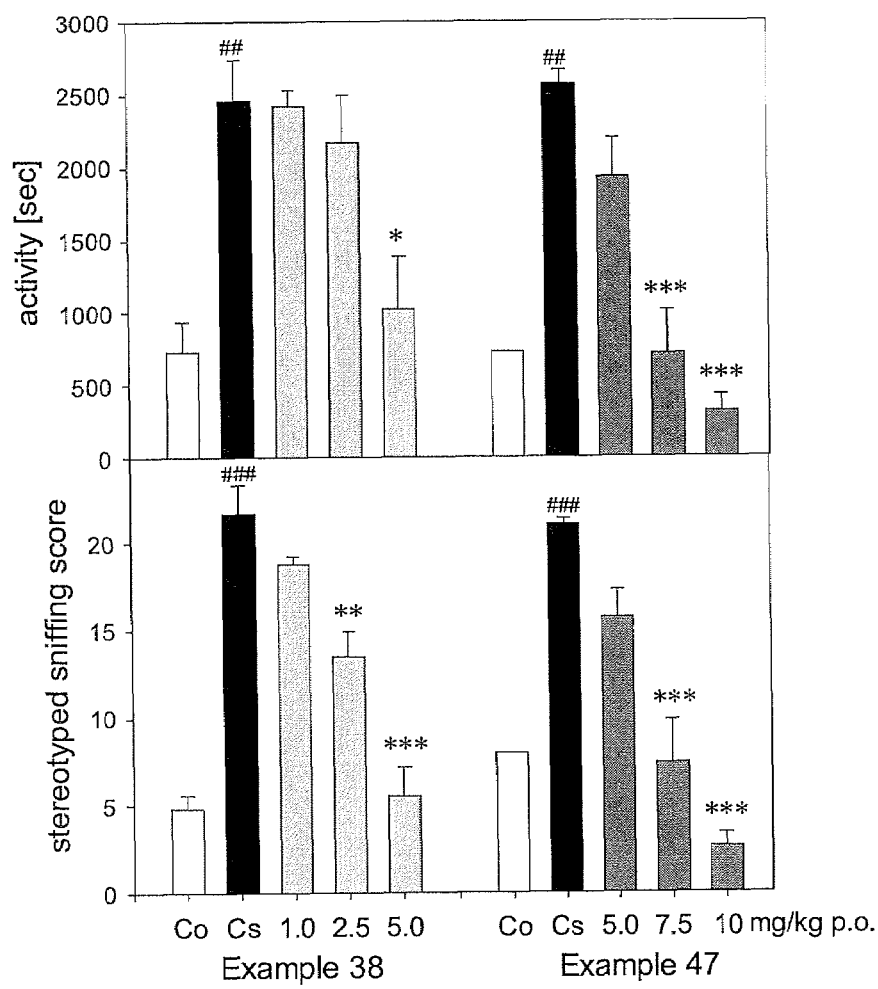
FIG. 6 shows the effect of the compounds of Example 38 and 47 on MK-801-induced psychosis.

FIG. 6 shows the effect of the compounds of Example 38 and 47 on MK-801-induced psychosis MK-801 at 0.1 mg/kg i.p. was administered 10 min before testing. Compounds at the described doses were administered 30 min prior to the test. Activity and stereotyped sniffing was recorded for 1 h. Co=control without MK-801 stimulation. Cs=control with MK-801 stimulation. Significant to non-stimulated control (Co): ## $p<0.01$, ### $p<0.001$. Significant to MK-801 stimulated control (Cs): * $p<0.05$,  $p<0.01$, * $p<0.001$.

Figure 7:
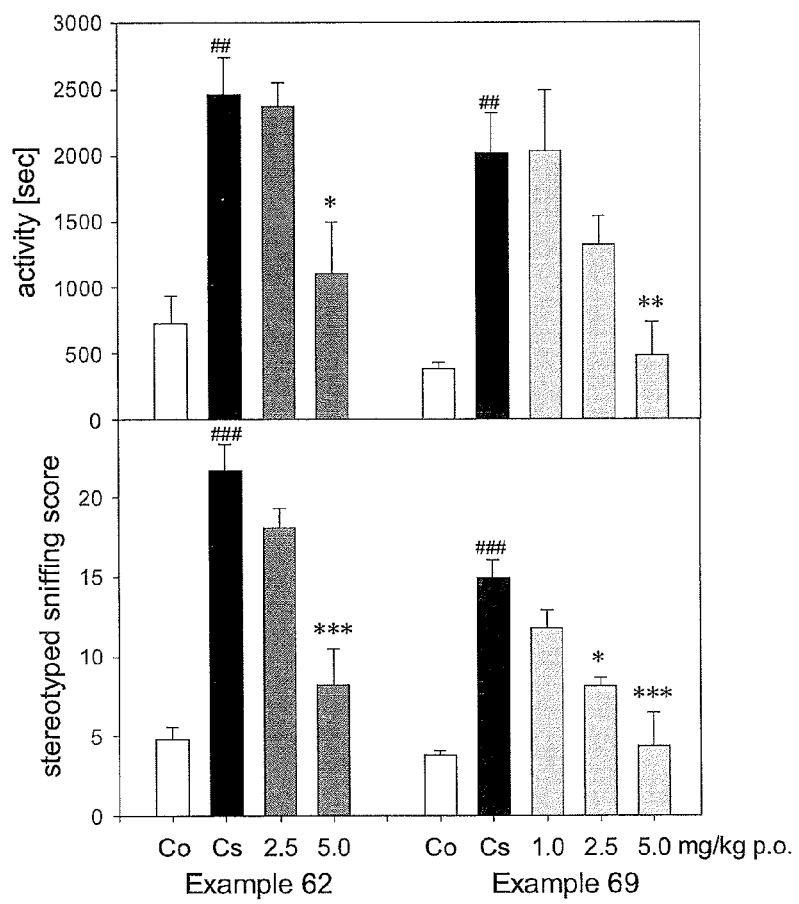
FIG. 7 shows the effect of the compounds of Example 62 and 69 on MK-801 induced psychosis.

FIG. 7 shows the effect of the compounds of Example 62 and 69 on MK-801-induced psychosis MK-801 at 0.1 mg/kg i.p. was administered 10 min before testing. Compounds at the described doses were administered 30 min prior to the test. Activity and stereotyped sniffing was recorded for 1 h. Co=control without MK-801 stimulation. Cs=control with MK-801 stimulation. Significant to non-stimulated control (Co): ## $p<0.01$, ### $p<0.001$. Significant to MK-801 stimulated control (Cs): * $p<0.05$,  $p<0.01$, * $p<0.001$.

Figure 8:
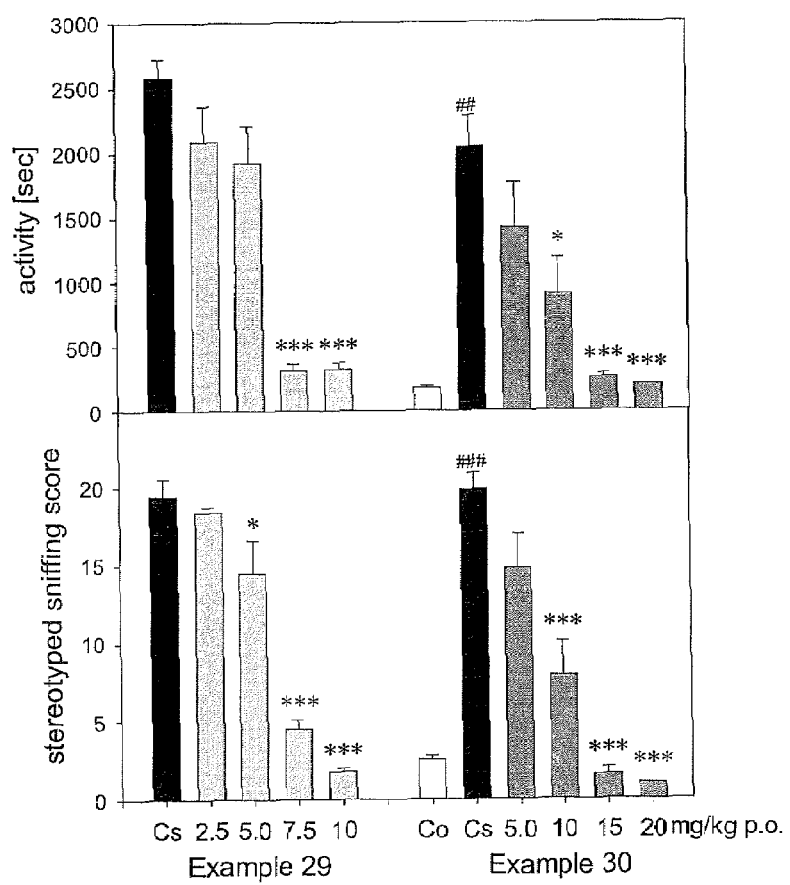
FIG. 8 shows the effect of the compounds of Example 24 and 30 on MK-801 induced psychosis.

FIG. 8 shows the effect of the compounds of Example 29 and 30 on MK-801-induced psychosis MK-801 at 0.1 mg/kg i.p. was administered 10 min before testing. Compounds at the described doses were administered 30 min prior to the test. Activity and stereotyped sniffing was recorded for 1 h. Co=control without MK-801 stimulation. Cs=control with MK-801 stimulation. Significant to non-stimulated control (Co): ## $p<0.01$, ### $p<0.001$. Significant to MK-801 stimulated control (Cs): * $p<0.05$, *** $p<0.001$.

The compound of Example 91 significantly reduced MK-801-induced hyperactivity and stereotyped sniffing starting at 15 mg/kg i.p. The compounds of Example 95 and 55 significantly reversed MK-801-induced hyperactivity and stereotyped sniffing at 30 mg/kg p.o. Example 35 significantly reversed MK-801-induced hyperactivity at 30 mg/kg and stereotyped sniffing starting at 30 mg/kg p.o. The compound of Example 30 significantly reversed MK-801-induced hyperactivity and stereotyped sniffing starting at 10 mg/kg p.o. The compound of Example 47 significantly reversed MK-801-induced hyperactivity and stereotyped sniffing starting at 7.5 mg/kg p.o. Example 29 significantly reversed MK-801-induced hyperactivity starting at 7.5 mg/kg and stereotyped sniffing starting at 5 mg/kg p.o. The compound of Example 62 significantly reversed MK-801-induced hyperactivity and stereotyped sniffing starting at 5 mg/kg p.o. The compounds of Example 38 and 69 significantly reversed MK-801-induced hyperactivity starting at 5.0 mg/kg and stereotyped sniffing starting at 2.5 mg/kg p.o. The results give evidence for the antipsychotic potential of the compounds.

The invention claimed is:

1. A compound of formula (II)

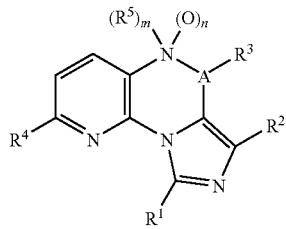

wherein the bond between A and N is a single bond or a double bond;
A is C when the bond is a double bond and CH when the bond is a single bond;
m is 0 or 1;
n is 0 or 1;
$R^1$ and $R^2$ are independently selected from
H,
a cyclic radical;
$C_{1-8}$ alkyl, optionally mono- or polysubstituted with at least one of halo, OH, O—$C_{1-3}$ alkyl or a cyclic radical;
$C_{2-8}$ alkenyl, optionally mono- or polysubstituted with at least one of halo, OH, O—$C_{1-3}$ alkyl or a cyclic radical;
$C_{2-8}$ alkynyl, optionally mono- or polysubstituted with at least one of halo, OH, O—$C_{1-3}$-alkyl or a cyclic radical;
a saturated, monounsaturated or polyunsaturated carbocycle ring system with 3 to 8 atoms or a heterocyclic ring with 5 to 15 ring atoms, each optionally mono- or polysubstituted with at least one of halo, amino, $C_{1-3}$ alkylamino, di-$C_{1-3}$ alkylamino, nitro, $C_{1-3}$ alkyl, O—$C_{1-3}$ alkyl or a cyclic radical; and
$R^3$ is selected from
H,
a cyclic radical,
$N_3$,
CN,
$R^6$, $OR^6$, $SR^6$, $SOR^6$, $SO_2R^6$,
NH(CO)$OR^6$, N((CO)$OR^6)_2$, $NR^6$((CO)$OR^6$),
NH—(C=O)—$NH_2$, $NR^6$—(C=O)—$NH_2$,
NH—(C=O)—$NHR^6$, $NR^6$—(C=O)—$NHR^6$,
NH—$SO_2R^6$, N($SO_2R^6)_2$ and $NR^6(SO_2R^6$),
wherein $R^6$ is independently,
a cyclic radical,
$C_{1-8}$ alkyl, $C_{3-8}$ cyclo(hetero)alkyl,
$C_{2-8}$ alkenyl, $C_{3-8}$ cyclo(hetero)alkenyl,
or $C_{2-8}$ alkynyl each optionally mono or polysubstituted with at least one of halo, OH, O—$C_{1-3}$ alkyl or a cyclic radical,
$R^7$, $OR^7$, $SR^7$, $NHSO_2R^7$, $N(SO_2R^7)$, or $N(R^8)SO_2R^7$, wherein $R^7$ is aryl, heteroaryl, aryl-$C_{1-5}$ alkyl, heteroaryl-$C_{1-5}$ alkyl,
wherein aryl is phenyl or naphthyl, heteroaryl is an aromatic heterocyclic ring system of 5 to 15 ring atoms containing at least one atom selected from N including N-oxide, S, and O and wherein aryl and heteroaryl are optionally mono- or polysubstituted with at least one of halo, amino, $C_{1-3}$ alkylamino, di-$C_{1-3}$ alkylamino, nitro, $C_{1-3}$ alkyl, O—$C_{1-3}$ alkyl or a cyclic radical and
$R^8$ is $C_{1-5}$ alkyl, optionally mono or polysubstituted with at last one of halo, OH, O—$C_{1-3}$ alkyl or a cyclic radical,
$R^4$ is selected from
H,
halo,
a cyclic radical,
$R^9$,
OH or $OR^9$,
NH(C=O)—$C_{1-3}$ alkyl, optionally mono- or polysubstituted with at least one of halo, OH, O—$C_{1-3}$ alkyl or a cyclic radical,
$NH_2$, $NHR^9$ or $NR^9R^{10}$,
wherein $R^9$ and $R^{10}$ are independently selected from a cyclic radical,
$C_{1-6}$ alkyl or $C_{3-6}$ cyclo(hetero)alkyl, optionally mono- or polysubstituted with at least one of halo, OH, O—$C_{1-3}$ alkyl or a cyclic radical,
aryl-$C_{1-5}$-alkyl wherein aryl is phenyl, optionally mono- or polysubstituted with at least one of halo, amino, $C_{1-3}$ alkylamino, di-$C_{1-3}$ alkylamino, nitro, $C_{1-3}$ alkyl, O—$C_{1-3}$ alkyl or a cyclic radical or
$NR^9R^{10}$ together form a saturated or unsaturated five-, six- or seven-membered ring which can contain up to 3 heteroatoms, preferably N including N-oxide, S or O, optionally mono- or polysubstituted with at least one of halo, amino, $C_{1-3}$ alkylamino, di-$C_{1-3}$ alkylamino, nitro, $C_{1-3}$ alkyl, O—$C_{1-3}$ alkyl or aryl-$C_{1-5}$-alkyl, wherein aryl is phenyl, optionally mono- or polysubstituted with at least one of halo, amino, $C_{1-3}$ alkylamino, di-$C_{1-3}$ alkylamino, nitro, $C_{1-3}$ alkyl, O—$C_{1-3}$ alkyl or a cyclic radical,
and $R^5$ is selected from
H,
$C_{1-5}$ alkyl, $C_{3-6}$ cycloalkyl or (CO)—$C_{1-5}$ alkyl, optionally mono or polysubstituted with at least one of halo, OH, O—$C_{1-3}$ alkyl or a cyclic radical,
or a pharmaceutically acceptable salt or prodrug thereof,
wherein if m and n are 1,
A and N are not a double bond;
wherein if m is 1 and n is O, A and N are not a double bond;
wherein if n is 1 and m is O, A and N are not a single bond; and
wherein if m and n are O, A and N are not a single bond.

2. A compound according to claim 1 wherein the bond between A and N is a double bond.

3. A compound according to claim 1 wherein m and n are both 0.

4. A compound according to claim 1, wherein $R^1$ is $C_{2-4}$ alkyl or phenyl each optionally substituted.

5. A compound according to 1, wherein $R^2$ is H, methyl or trifluoromethyl.

6. A compound according to claim 1 wherein $R^3$ is H, —CN or $C_{1-3}$ alkyl.

7. A compound according to claim 1, wherein $R^3$ is —NH—(C=O)—$OR^6$.

8. A compound according to claim 1, wherein $R^3$ is —NH—$SO_2R^6$.

9. A compound according to claim 1, wherein $R^4$ is H, $C_{1-3}$ alkyl or O—$C_{1-3}$ alkyl each optionally substituted.

10. A compound according to claim 1 selected from the group consisting of 4,8-dimethoxy-3-methyl-1-propyl-imidazo[1,5-a]pyrido[3,2-e]pyrazine;
- 4,8-dimethoxy-1-propyl-imidazo[1,5-a]pyrido[3,2-e]pyrazine;
- 4,8-dimethoxy-1-ethyl-3-methyl-imidazo[1,5-a]pyrido[3,2-e]pyrazine;
- 4,8-dimethoxy-1,3-dimethyl-imidazo[1,5-a]pyrido[3,2-e]pyrazine;
- 4,8-dimethoxy-3-methyl-imidazo[1,5-a]pyrido[3,2-e]pyrazine;
- 1-ethyl-4-isopropyloxy-8-methoxy-3-methyl-imidazo[1,5-a]pyrido[3,2-e]pyrazine;
- 1-ethyl-8-methoxy-3-methyl-4-propyloxy-imidazo[1,5-a]pyrido[3,2-e]pyrazine;
- 4-cyclopentyloxy-1-ethyl-8-methoxy-3-methyl-imidazo[1,5-a]pyrido[3,2-e]pyrazine;
- 4-isopropyloxy-8-methoxy-3-methyl-1-propyl-imidazo[1,5-a]pyrido[3,2-e]pyrazine;
- 8-methoxy-1,3-dimethyl-4-(2,3,6-trifluorobenzyloxy)-imidazo[1,5-a]pyrido[3,2-e]pyrazine;
- 4-(2,4-dichlorobenzyloxy)-1-ethyl-8-methoxy-3-methyl-imidazo[1,5-a]pyrido[3,2-e]pyrazine;
- 4-(2-chloro-6-fluorobenzyloxy)-1-ethyl-8-methoxy-3-methyl-imidazo[1,5-a]pyrido[3,2-e]pyrazine;
- 1-ethyl-8-methoxy-3-methyl-4-(2,3,6-trifluorobenzyloxy)-imidazo[1,5-a]pyrido[3,2-e]pyrazine;
- 1-ethyl-8-methoxy-3-methyl-4-(2,4,6-trimethylbenzyloxy)-imidazo[1,5-a]pyrido[3,2-e]pyrazine;
- 4-(2-chloro-6-fluorobenzyloxy)-8-methoxy-3-methyl-1-propyl-imidazo[1,5-a]pyrido[3,2-e]pyrazine;
- 4-(2,6-difluorobenzyloxy)-8-methoxy-3-methyl-1-propyl-imidazo[1,5-a]pyrido[3,2-e]pyrazine;
- 1-ethyl-8-methoxy-3-methyl-4-(2-phenylethyloxy)-imidazo[1,5-a]pyrido[3,2-e]pyrazine;
- 8-methoxy-3-methyl-4-(2-phenylethyloxy)-1-propyl-imidazo[1,5-a]pyrido[3,2-e]pyrazine;
- 8-methoxy-1,3-dimethyl-4-(2-phenylethyloxy)-imidazo[1,5-a]pyrido[3,2-e]pyrazine;
- 8-methoxy-3-methyl-4-(2-phenylethyloxy)-imidazo[1,5-a]pyrido[3,2-e]pyrazine;
- 8-methoxy-3-methyl-4-(3-phenylpropyloxy)-1-propyl-imidazo[1,5-a]pyrido[3,2-e]pyrazine;
- 1-ethyl-8-methoxy-3-methyl-4-(3-phenylpropyloxy)-imidazo[1,5-a]pyrido[3,2-e]pyrazine;
- 1,3-dimethyl-8-methoxy-4-(3-phenylpropyloxy)-imidazo[1,5-a]pyrido[3,2-e]pyrazine;
- 4-[(3,5-dimethylisoxazol-4-yl)methyloxy]-1-ethyl-8-methoxy-3-methyl-imidazo[1,5-a]pyrido[3,2-e]pyrazine;
- 1-ethyl-8-methoxy-3-methyl-4-methylthio-imidazo[1,5-a]pyrido[3,2-e]pyrazine;
- 8-methoxy-3-methyl-4-methylthio-1-propyl-imidazo[1,5-a]pyrido[3,2-e]pyrazine;
- 1,3-dimethyl-8-methoxy-4-methylthio-imidazo[1,5-a]pyrido[3,2-e]pyrazine;
- 8-methoxy-3-methyl-4-methylthio-imidazo[1,5-a]pyrido[3,2-e]pyrazine;
- 4-cyano-8-methoxy-3-methyl-1-propyl-imidazo[1,5-a]pyrido[3,2-e]pyrazine;
- 4-cyano-8-methoxy-3-methyl-1-ethyl-imidazo[1,5-a]pyrido[3,2-e]pyrazine;
- 4-azido-8-methoxy-3-methyl-1-propyl-imidazo[1,5-a]pyrido[3,2-e]pyrazine;
- 8-methoxy-3-methyl-4-methylsulfinyl-1-propyl-imidazo[1,5-a]pyrido[3,2-e]pyrazine;
- 8-methoxy-3-methyl-4-methylsulfonyl-1-propyl-imidazo[1,5-a]pyrido[3,2-e]pyrazine;
- 1-ethyl-8-methoxy-3-methyl-4-methylsulfinyl-imidazo[1,5-a]pyrido[3,2-e]pyrazine;
- 8-methoxy-3-methyl-1-propyl-imidazo[1,5-a]pyrido[3,2-e]pyrazine;
- 1-ethyl-8-methoxy-3-methyl-imidazo[1,5-a]pyrido[3,2-e]pyrazine;
- 4-ethyl-8-methoxy-3-methyl-1-propyl-imidazo[1,5-a]pyrido[3,2-e]pyrazine;
- 3,4-dimethyl-8-methoxy-1-propyl-imidazo[1,5-a]pyrido[3,2-e]pyrazine;
- 3,4-dimethyl-8-methoxy-1-propyl-imidazo[1,5-a]pyrido[3,2-e]pyrazine hydrochloride;
- 1-ethyl-3,4-dimethyl-8-methoxy-imidazo[1,5-a]pyrido[3,2-e]pyrazine;
- 1,3,4-trimethyl-8-methoxy-imidazo[1,5-a]pyrido[3,2-e]pyrazine;
- 3,4-dimethyl-8-methoxy-1-(3,3,3-trifluoropropyl)-imidazo[1,5-a]pyrido[3,2-e]pyrazine;
- 3,4-dimethyl-8-methoxy-1-pentyl-imidazo[1,5-a]pyrido[3,2-e]pyrazine;
- 1-cyclohexyl-3,4-dimethyl-8-methoxy-imidazo[1,5-a]pyrido[3,2-e]pyrazine;
- 3,4-dimethyl-1-hexyl-8-methoxy-imidazo[1,5-a]pyrido[3,2-e]pyrazine;
- 3,4-dimethyl-8-methoxy-1-phenethyl-imidazo[1,5-a]pyrido[3,2-e]pyrazine;
- 3,4-dimethyl-8-methoxy-1-phenyl-imidazo[1,5-a]pyrido[3,2-e]pyrazine;
- 3,4-dimethyl-8-methoxy-1-phenyl-imidazo[1,5-a]pyrido[3,2-e]pyrazine dihydrochloride;
- 3,4-dimethyl-8-methoxy-1-(2-chlorophenyl)-imidazo[1,5-a]pyrido[3,2-e]pyrazine;
- 3,4-dimethyl-8-methoxy-1-(4-fluorophenyl)-imidazo[1,5-a]pyrido[3,2-e]pyrazine;
- 1-propyl-3,4,8-trimethyl-imidazo[1,5-a]pyrido[3,2-e]pyrazine;
- 1-propyl-3,4-dimethyl-imidazo[1,5-a]pyrido[3,2-e]pyrazine;
- 1-propyl-4,8-dimethyl-imidazo[1,5-a]pyrido[3,2-e]pyrazine;
- 8-difluoromethoxy-3,4-dimethyl-1-propyl-imidazo[1,5-a]pyrido[3,2-e]pyrazine;
- 3,4-dimethyl-8-(piperidin-1-yl)-methoxy-1-propyl-imidazo[1,5-a]pyrido[3,2-e]pyrazine;
- 3,4-dimethyl-8-(4-methyl-piperazin-1-yl)-methoxy-1-propyl-imidazo[1,5-a]pyrido[3,2-e]pyrazine;
- 3,4-dimethyl-8-(2-ethyl-4-methyl-imidazol-1-yl)-methoxy-1-propyl-imidazo[1,5-a]pyrido[3,2-e]pyrazine;

3,4-dimethyl-8-(2-propyl-4-methyl-imidazol-1-yl)-methoxy-1-propyl-imidazo[1,5-a]pyrido[3,2-e]pyrazine;

4-difluoromethoxy-3-methyl-1-propyl-imidazo[1,5-a]pyrido[3,2-e]pyrazine-8-ol 8-methoxy-3-methyl-5-oxo-1-propyl-imidazo[1,5-a]pyrido[3,2-e]pyrazine;

3,4-dimethyl-8-methoxy-5-oxo-1-propyl-imidazo[1,5-a]pyrido[3,2-e]pyrazine;

8-methoxy-4-methoxycarbonylamino-3-methyl-1-propyl-imidazo[1,5-a]pyrido[3,2-e]pyrazine;

4-ethoxycarbonylamino-8-methoxy-3-methyl-1-propyl-imidazo[1,5-a]pyrido[3,2-e]pyrazine;

4-(N,N-bis-methoxycarbonyl)-amino-8-methoxy-3-methyl-1-propyl-imidazo[1,5-a]pyrido[3,2-e]pyrazine;

8-methoxy-4-(methoxycarbonyl-methyl-amino)-3-methyl-1-propyl-imidazo[1,5-a]pyrido[3,2-e]pyrazine;

8-methoxy-3-methyl-4-(3-methyl-ureido)-1-propyl-imidazo[1,5-a]pyrido[3,2-e]pyrazine;

8-methoxy-3-methyl-1-propyl-4-ureido-imidazo[1,5-a]pyrido[3,2-e]pyrazine;

8-methoxy-3-methyl-4-(3-isopropyl-ureido)-1-propyl-imidazo[1,5-a]pyrido[3,2-e]pyrazine;

8-methoxy-3-methyl-4-methylsulfonylamino-1-propyl-imidazo[1,5-a]pyrido[3,2-e]pyrazine;

4-(N,N-bis-methylsulfonyl)-amino-8-methoxy-3-methyl-1-propyl-imidazo[1,5-a]pyrido[3,2-e]pyrazine;

4-ethylsulfonylamino-8-methoxy-3-methyl-1-propyl-imidazo[1,5-a]pyrido[3,2-e]pyrazine;

1-ethyl-8-methoxy-3-methyl-4-methylsulfonylamino-imidazo[1,5-a]pyrido[3,2-e]pyrazine;

8-methoxy-3-methyl-1-propyl-4-trifluoromethylsulfonylamino-imidazo[1,5-a]pyrido[3,2-e]pyrazine;

8-methoxy-3-methyl-1-propyl-4-propylsulfonylamino-imidazo[1,5-a]pyrido[3,2-e]pyrazine;

4-isopropylsulfonylamino-8-methoxy-3-methyl-1-propyl-imidazo[1,5-a]pyrido[3,2-e]pyrazine;

8-methoxy-3-methyl-4-(4-methylphenylsulfonylamino)-1-propyl-imidazo[1,5-a]pyrido[3,2-e]pyrazine;

4-[N,N-bis-(4-methylphenylsulfonyl)-amino]-8-methoxy-3-methyl-1-propyl-imidazo[1,5-a]pyrido[3,2-e]pyrazine;

8-methoxy-3-methyl-1-(3,3,3-trifluoropropyl)-4-methylsulfonylamino-imidazo[1,5-a]pyrido[3,2-e]pyrazine;

1-hexyl-8-methoxy-3-methyl-4-methylsulfonylamino-imidazo[1,5-a]pyrido[3,2-e]pyrazine;

8-methoxy-3-methyl-1-phenethyl-4-methylsulfonylamino-imidazo[1,5-a]pyrido[3,2-e]pyrazine;

8-methoxy-3-methyl-1-phenyl-4-methylsulfonylamino-imidazo[1,5-a]pyrido[3,2-e]pyrazine;

1-(2-chlorophenyl)-8-methoxy-3-methyl-4-methylsulfonylamino-imidazo[1,5-a]pyrido[3,2-e]pyrazine;

1-(4-fluorophenyl)-8-methoxy-3-methyl-4-methylsulfonylamino-imidazo[1,5-a]pyrido[3,2-e]pyrazine;

3-methyl-8-(4-methyl-2-propyl-imidazol-1-yl)-1-propyl-4-methylsulfonylamino-imidazo[1,5-a]pyrido[3,2-e]pyrazine;

3-methyl-4-methylsulfonylamino-1-propyl-imidazo[1,5-a]pyrido[3,2-e]pyrazin-8-ol hydrobromide;

3-methyl-4-methylsulfonylamino-1-propyl-imidazo[1,5-a]pyrido[3,2-e]pyrazin-8-ol;

8-difluoromethoxy-3-methyl-4-methylsulfonylamino-1-propyl-imidazo[1,5-a]pyrido[3,2-e]pyrazine;

8-cyclopropylmethoxy-3-methyl-4-methylsulfonylamino-1-propyl-imidazo[1,5-a]pyrido[3,2-e]pyrazine;

3-methyl-1-propyl-4,5-dihydro-imidazo[1,5-a]pyrido[3,2-e]pyrazine;

8-methoxy-1-propyl-4,5-dihydro-imidazo[1,5-a]pyrido[3,2-e]pyrazine;

8-methoxy-3-methyl-1-propyl-4,5-dihydro-imidazo[1,5-a]pyrido[3,2-e]pyrazine;

8-methoxy-3-methyl-1-propyl-4,5-dihydro-imidazo[1,5-a]pyrido[3,2-e]pyrazine hydrochloride;

1-ethyl-8-methoxy-3-methyl-4,5-dihydro-imidazo[1,5-a]pyrido[3,2-e]pyrazine;

3,5-dimethyl-8-methoxy-1-propyl-4,5-dihydro-imidazo[1,5-a]pyrido[3,2-e]pyrazine;

5-acetyl-8-methoxy-3-methyl-1-propyl-4,5-dihydro-imidazo[1,5-a]pyrido[3,2-e]pyrazine;

or a pharmaceutically acceptable salt or prodrug thereof.

11. A pharmaceutical composition comprising a compound of claim 1 and at least one of a pharmaceutically acceptable carrier, diluent or adjuvant.

* * * * *

SEQUENCE LISTING

<160> NUMBER OF SEQ ID NOS: 7

<210> SEQ ID NO 1
<211> LENGTH: 26
<212> TYPE: DNA
<213> ORGANISM: Artificial
<220> FEATURE:
<223> OTHER INFORMATION: Primer P1
<220> FEATURE:
<221> NAME/KEY: primer_bind
<222> LOCATION: (1)..(26)

<400> SEQUENCE: 1
tgcatctaca gggttaccat ggagaa                                   26

<210> SEQ ID NO 2
<211> LENGTH: 29
<212> TYPE: DNA
<213> ORGANISM: Artificial
<220> FEATURE:
<223> OTHER INFORMATION: Primer P2
<220> FEATURE:
<221> NAME/KEY: primer_bind
<222> LOCATION: (1)..(29)

<400> SEQUENCE: 2
tatccctgca ggccttcagc agaggctct                                29

<210> SEQ ID NO 3
<211> LENGTH: 28
<212> TYPE: DNA
<213> ORGANISM: Artificial
<220> FEATURE:
<223> OTHER INFORMATION: Primer P3
<220> FEATURE:
<221> NAME/KEY: primer_bind
<222> LOCATION: (1)..(28)

<400> SEQUENCE: 3
ttcacatgga tatgcgacgg taccttct                                 28

<210> SEQ ID NO 4
<211> LENGTH: 31
<212> TYPE: DNA
<213> ORGANISM: Artificial
<220> FEATURE:
<223> OTHER INFORMATION: Primer P4
<220> FEATURE:
<221> NAME/KEY: primer_bind
<222> LOCATION: (1)..(31)

<400> SEQUENCE: 4
ctgtgaagaa gaactatcgg cgggttcctt a                             31

<210> SEQ ID NO 5
<211> LENGTH: 967
<212> TYPE: DNA
<213> ORGANISM: pig
<220> FEATURE:
<221> NAME/KEY: misc_feature
<222> LOCATION: (1)..(967)
<223> OTHER INFORMATION: pig: priming with P1 and P2

<400> SEQUENCE: 5
tgcatctaca gggttaccat ggagaagctg tcctaccaca gcatttgtac cgcggaagag     60
tggcaaggcc tcatgcgctt caaccttccc gtccgtcttt gcaaggagat tgaattgttc    120

```
cacttcgaca ttggtccttt tgaaaacatg tggcctggaa tctttgtcta tatggttcat      180
cgcttctgtg ggacggcctg ctttgagctt gaaaagctgt gtcgttttat catgtctgtg      240
aagaagaact atcgtcgggt tccttaccac aactggaagc acgcggtcac ggtggcacac      300
tgcatgtacg ccatcctcca gaacagccac gggctcttca ccgacctcga gcgcaaagga      360
ctgctaatcg cgtgtctgtg ccacgacctg gaccacaggg gcttcagcaa cagctacctg      420
cagaaattcg accacccct ggccgctctc tactccacgc ccaccatgga gcagcaccac       480
ttctcccaga ccgtgtccat cctccagttg aagggcaca acatcttctc caccctgagc       540
tccagtgagt acgagcaggt gcttgagatc atccgcaaag ccatcattgc cacagacctc      600
gctttgtact ttggaaacag gaaacagttg gaggagatgt accagaccgg atcgctaaac      660
cttaataacc agtcacatag agaccgcgtc attggtttga tgatgactgc ctgtgatctc      720
tgttccgtga caaaactgtg gccagtaaca aaactgacgg caaatgatat atatgcggaa      780
ttctgggccg agggcgatga ggtgaagaag ctgggaatac agcctattcc catgatggac      840
agagacaaga aggacgaagt cccacaaggc cagctcggat tctacaacgc ggtagctatc      900
ccctgctaca ccaccctcac ccagatcttc ccgcccacag agcctcttct gaaggcctgc      960
agggata                                                                967

<210> SEQ ID NO 6
<211> LENGTH: 732
<212> TYPE: DNA
<213> ORGANISM: guinea pig
<220> FEATURE:
<221> NAME/KEY: misc_feature
<222> LOCATION: (1)..(732)
<223> OTHER INFORMATION: guinea pig: priming with P4 and P2

<400> SEQUENCE: 6
ctgtgaagaa gaactatcgg cgggttcctt accacaactg gaagcatgca gtcacggtgg       60
cgcactgcat gtacgccata cttcaaaaca acaatggcct cttcacagac cttgagcgca      120
aaggcctgct aattgcctgt ctgtgccatg acctggacca caggggcttc agtaacagct      180
acctgcagaa attcgaccac cccctggctg cgttgtactc cacctccacc atggagcaac      240
accacttctc ccagacggtg ttcatcctcc agctggaagg acacaacatc ttctccaccc      300
tgagctccag cgagtacgag caggtgctgg agatcatccg caaagccatc atcgccactg      360
acctcgcact gtactttggg aacaggaagc agttggagga gatgtaccag acagggtcgc      420
tgaacctcaa taaccagtcc catcgagacc gcgtcatcgg cttgatgatg actgcctgcg      480
atctttgctc tgtgacgaaa ctatggccag ttacaaaatt gacagcaaat gatatatatg      540
cagagttctg ggctgagggg gatgagatga agaagttggg gatacagccc atccctatga      600
tggacagaga caagaaggat gaagtccctc aaggacagct tggattctac aatgctgtgg      660
ccatcccctg ctataccacc ctgacgcaga tcctcccacc cacagagcct ctgctgaagg      720
cctgcaggga ta                                                          732

<210> SEQ ID NO 7
<211> LENGTH: 266
<212> TYPE: DNA
<213> ORGANISM: guinea pig
<220> FEATURE:
<221> NAME/KEY: misc_feature
<222> LOCATION: (1)..(266)
<223> OTHER INFORMATION: guinea pig: priming with P2 and P3
```

-continued

```
<400> SEQUENCE: 7
tagagcctct gctgaaggcc tgcagggata acctcaatca gtgggagaag gtaattcgag      60
gggaagagac agcaatgtgg atttcaggcc cagcaactag caaaagcaca tcagggaagc     120
cgaccaggaa ggtcgatgac tgatcctgag gtgatgtctg cctagcaact gactcaacct     180
gcttctgtga cttcgttctt tttattttta ttttttttaac ggggtgaaaa cctctctcag    240
aaggtaccgt cgcatatcca tgtgaa                                          266
```